(12) United States Patent
Rittershaus et al.

(10) Patent No.: US 6,555,113 B1
(45) Date of Patent: *Apr. 29, 2003

(54) MODULATION OF CHOLESTERYL ESTER TRANSFER PROTEIN (CETP) ACTIVITY

(75) Inventors: Charles W. Rittershaus, Malden, MA (US); Lawrence J. Thomas, Worcester, MA (US)

(73) Assignee: AVANT Immunotherapeutics, Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/945,289

(22) PCT Filed: May 1, 1996

(86) PCT No.: PCT/US96/06147

§ 371 (c)(1),
(2), (4) Date: Oct. 17, 1997

(87) PCT Pub. No.: WO96/34888

PCT Pub. Date: Nov. 7, 1996

Related U.S. Application Data

(63) Continuation-in-part of application No. 08/432,483, filed on May 1, 1995, now Pat. No. 6,410,022.

(51) Int. Cl.[7] ............................................. A61K 39/385
(52) U.S. Cl. ................................ 424/193.1; 424/185.1; 424/146.1
(58) Field of Search ........................... 424/185.1, 193.1, 424/146.1; 435/193, 68.1; 530/350, 402, 403

(56) References Cited

U.S. PATENT DOCUMENTS

| | | | |
|---|---|---|---|
| 5,242,687 A | 9/1993 | Tykocinskli et al. | |
| 5,338,829 A | 8/1994 | Weiner et al. | |
| 5,705,388 A | 1/1998 | Couture et al. | |
| 5,843,446 A | * 12/1998 | Ladd et al. | |
| 6,143,305 A | * 11/2000 | Stevens | 424/195.11 |

FOREIGN PATENT DOCUMENTS

| | | | | |
|---|---|---|---|---|
| EP | 0 343 460 A2 | 11/1989 | ............ | C07K/7/08 |
| EP | 752 886 B1 | 1/1998 | | |
| WO | WO 90/15627 | 12/1990 | ........... | A61K/47/48 |
| WO | WO 92/10203 | 6/1992 | ........... | A61K/37/22 |
| WO | WO 93/11782 | 6/1993 | ........... | A61K/37/00 |
| WO | WO 93/23076 | 11/1993 | ........... | A61K/39/00 |
| WO | WO 94/24567 | 10/1994 | ........... | G01N/33/92 |
| WO | WO 94/25060 | 11/1994 | ........... | A61K/37/38 |
| WO | WO 95/05849 | 3/1995 | | |
| WO | WO 96/39168 | 12/1996 | ........... | A61K/38/17 |

OTHER PUBLICATIONS

Smith et al. Med. Sci. Research 21: 911, 1993.*
Albers et al., *Arteriosclerosis*, 4: 49–58 (1984).
Alberts et al., *Molecular Biology of the Cell*, $2^{nd}$ ed., (Garland Publishing, Inc., New York, NY., 1989) pp. 1006–1007.
Alexander et al., *Immunity*, 1: 751–761 (1994).
Barter et al., *J. Lipid Res.*, 21:238–249 (1980).
Bevilacqua et al., *J. Clin. Invest.*, 91: 379–387 (1993).
Bisgaier et al., *J. Lipid Res.*, 34: 1625–1634 (1991).
Bisgaier et al., *J. Lipid Res.*, 32: 21–23 (1993).
Breslow, *Proc. Natl. Acad. Sci.* USA, 90: 8314–8318 (1993).
Brown et al., *Nature*, 342: 448–451 (1989).
Carlsson et al., *Biochem. J.*, 173: 723–737 (1978).
Casali et al., *Science*, 234: 476–479 (1986).
Castelli et al., *J. Am. Med. Assoc.*, 256: 2835–2838 (1986).
Davis et al., *Microbiology*, $2^{nd}$ ed., (Harper & Row, Publishers, Hagerstown, Maryland, 1973), pp. 354–356.
Drayna et al., *Nature*, 327: 632–634 (1987).
Elridge et al., *Immunology of Proteins and Peptides V: Vaccines; Mechanisms, Designs, and Applications*, Attasi, M.Z., ed. (Plenum Press, New York, 1989), pp. 191–202.
Engelhard, Victor H., *Sci. Am.*, 54–60 (1994).
Etlinger et al., *Science*, 249: 423–425 (1990).
Etlinger H., *Immunol. Today*, 13: 52–55 (1992).
Fielding et al., *J. Lipid Res.*, 36: 211–228 (1995).
Frondorf et al., *J. Immunol.* Methods, 172: 135–137 (1994).
Gavish et al., *J. Lipid Res.*, 28: 257–267 (1987).
Gaynor et al., *Atheroscelorosis*, 110: 101–109 (1994).
*Genetic Engineering News*, 14: 44 (Aug. 1994).
Gordon et al., *N. Engl. J. Med.*, 321: 1311–1316 (1989).
Green et al., *Cell*, 28: 477–487 (1982).
Greenspan & Baxter, eds., *Basic and Clinical Endocrinology* 4ed., (Appleton & Lange, Inc. Norwalk, Connecticut, 1994), p. 432 (referring to the specifics of gonadotropin–releasing hormone).
Ha et al., *Comp. Biochem. Physiol.*, 83B: 463–466 (1986).
Ha et al., *Biochim. Biophys. Acta*, 833: 203–211 (1985).
Havel et al., Introduction: Structure and metabolism of plasma lipoproteins', In *The Metabolic Basis of Inherited Disease*, $6^{th}$ ed., pp. 1129–1138 (Scriver, C.R., et al., eds.) (McGraw–Hill, Inc., NewYork, 1989).

(List continued on next page.)

Primary Examiner—Patrick J. Nolan
(74) Attorney, Agent, or Firm—Leon R. Yankwich; Thomas R. Berka

(57) ABSTRACT

Conjugates are disclosed comprising a broad range helper T cell epitope portion and a B cell epitope portion from a cholesteryl ester transfer protein (CETP), which conjugates are capable of eliciting an immune response in an individual against the individual's endogenous CETP activity. The conjugates are useful in methods to inhibit CETP activity, to raise serum levels of high density lipoproteins, and to prevent or treat cardiovascular disease, such as atherosclerosis.

11 Claims, 12 Drawing Sheets

OTHER PUBLICATIONS

Hayek et al., *J. Clin. Invest.*, 90: 505–510 (1992).
Hayek et al., *J. Clin. Invest.*, 91: 1665–1671 (1993).
Hesler et al., *J. Biol. Chem.*, 263: 5020–5023 (1988).
Hesler et al., *J. Biol. Chem.*, 262: 2275–2282 (1987).
Holde et al., *Biochemistry*, pp. 626–630 (1990).
Ikewaki et al., *J. Clin. Invest.*, 96: 1573–1581 (1995).
Inazu et al., *N. Engl. J. Med.*, 323: 1234–1238.
Jarnagin et al., *Proc. Natl. Acad. Sci.* USA, 84: 1854–1857 (1987).
Jiang et al., *J. Biol. Chem.*, 266: 4631–4639 (1991).
Jiang et al., *J. Biol. Chem.*, 268: 27406–27412 (1991).
Kligfield et al., *Am. Heart J.*, 112(3): 589–597 (1986).
Korn et al., *J. Mol. Biol.*, 65: 525–529 (1972).
Kushwaha et al., *J. Lipid Res.*, 34: 1285–1297 (1993).
Madden et al., *Ann. Rev. Immunol.*, 13: 587–622 (1995).
Mader, S.S., In *Human Biology*, $4^{th}$ ed., pp. 83, 102 (Wm. C. Brown Publishers, Dubuque, Iowa, 1995).
Marguerite et al., *Mol. Immunol.*, 29: 793–800.
Marotti et al., *Nature*, 364: 73–75 (1993).
Mathews, C.K. and van Holde, K.E., *Biochemistry*, pp. 574–576, 626–630 (The Benjamin/Cummings Publishing Co., Redwood City, California, 1990).
Means and Feeney, *Bioconjugate Chem.*, 1: 2–12 (1990).
Mezdour et al., *Clin. Chem.* 40/4: 593–597 (1994).
Miller et al., *Am. Heart J.*, 113: 589–597 (1987).
Nagashima et al., *J. Lipid Res.*, 29: 1643–1649.
Nelson et al., *J. Clin. Invest.*, 91: 1157–1166 (1993).
Palker et al., *Proc. Natl. Acad. Sci.*, USA, 84: 2479–2483 (1987).
Panina–Bordignon et al., *Eur. J. Immunol.*, 19: 2237–2242 (1989).
Pruitt et al., *Transplantation*, 52: 868–873 (1991).
Pruitt et al., *J. Surg. Res.*, 50: 350–355 (1991).
Quig et al., *Ann. Rev. Nutr.*, 10: 169–193 (1990).
Quinet et al., *J. Clin. Invest.*, 85: 357–363 (1990).
Raju et al., *Eur. J. Immunol.*, 25: 3207–3214 (1995).
Rye et al., *J. Biol. Chem.*, 270: 189–196 (1995).
Sad et al., *Immunol.*, 76: 599–603 (1992).
Stern et al., *Nature*, 368: 215–221 (1994).
Suckling, Keith E., *Bio/Technology*, 12: 1379–1380 (1994).
Swenson et al., *J. Biol. Chem.*, 264: 14318–14326 (1989).
Swenson et al., *J. Biol. Chem.*, 263: 5150–5157 (1988).
Tall, A.R., *J. Lipid Res.*, 34: 1255–1274 (1993).
Tall, A.R., *J. Clin. Invest.*, 89: 379–384 (1990).
Tall, A.R., *J. Internal Med.*, 237: 5–12 (1995).
Talwar et al., *Proc. Natl. Acad. Sci.* USA, 91: 8532–8536 (1994).
Tam, J.P., *Proc. Natl. Acad. Sci.*, USA, 85: 5409–5413 (1988).
Tao et al., *Nature*, 362: 755–758 (1993).
Tato et al., *Arterioscler.Thromb. Vascular Biol.*, 15: 112–120 (1995).
*The Merck Manual of Diagnosis and Therapy*, $16^{th}$ ed., (Merck & Company, Inc., Rahway, New Jersey, 1992), pp. 22–23 (referring to infection prevention), pp. 114–115 (referring to bacterial diseases), pp. 1944–1947 (referring to health management of neonates, infants, and children).
Travis, *Science*, 262: 1974–1975 (1993).
Valmori et al., *J. Immunol.*, 149: 717–721 (1992).
Wang et al., *J. Biol. Chem.*, 270: 612–618 (1995).
Wang et al., *Science*, 254: 285–288 (1991).
Wang et al., *J. Biol. Chem.*, 268: 1955–1959 (1993).
Wang et al., *J. Biol. Chem.*, 267: 17487–17490 (1992).
Watanabe et al., *Proc. Natl. Acad. Sci.* USA, 89: 5103–5107 (1992).
Watson et al., *Molecular Biology of the Gene*, $4^{th}$ ed., (The Benjamin/Cummings Publishing Company, Inc., Melo Park, CA., 1987) p. 836.
Wedrychowski et al., *Biotechnology*, 11(4): 486–489 (1993).
Weisman et al., *Science*, 249: 146–151 (1990).
Whitlock et al., *J. Clin. Invest.*, 84:129–137 (1989).
Yeh et al., *J. Immunol.*, 146: 250–256 (1991).
Yen et al., *J. Clin. Invest.*, 83: 2018–2024 (1989).
Zannis et al., "Genetic mutations affecting human lipoproteins, their receptors, and their enzymes", In *Advances in Human Genetics, vol. 21*, pp. 145–319 (Plenum Press, New York, NY., 1993).
Zegers et al., *Eur. J. Immunol.*, 23: 630–634 (1993).

* cited by examiner

MODULATION OF CHOLESTERYL ESTER TRANSFER PROTEIN (CETP) ACTIVITY

This application is the U.S. national stage of international application No. PCT/US96/06147, filed May 1, 1996, and is a continuation-in-part of U.S. application Ser. No. 08/432,483, now U.S. Pat. No. 6,410,022, filed May 1, 1995.

GENERAL FIELD OF THE INVENTION

This invention is generally in the field of peptide-based vaccines to control treat, or reduce the risk of atherogenic activity in the circulatory system of humans and other animals. In particular, this invention provides compositions and methods for providing means to inhibit the activity of endogenous cholesteryl ester transfer protein (CETP) to treat cardiovascular disease prophylactically or therapeutically or to modulate the relative levels of lipoproteins to produce a condition correlated with a reduced risk of cardiovascular disease, such as atherosclerosis.

BACKGROUND OF THE INVENTION

Cholesterol circulates through the body predominantly as components of lipoprotein particles (lipoproteins), which are composed of a protein portion, called apolipoproteins (Apo) and various lipids, including phospholipids, triglycerides, cholesterol and cholesteryl esters. There are ten major classes of apolipoproteins: Apo A-I, Apo A-II, Apo-IV, Apo B-48, Apo B-100, Apo C-I, Apo C-II, Apo C-III, Apo D, and Apo E. Lipoproteins are classified by density and composition. For example, high density lipoproteins (HDL), one function of which is to mediate transport of cholesterol from peripheral tissues to the liver, have a density usually in the range of approximately 1.063–1.21 g/mL HDl. contain various amounts of Apo A-I, Apo A-II, Apo C-I, Apo C-II, Apo C-III, Apo D, Apo E, as well as various amounts of lipids, such as cholesterol, cholesteryl esters, phospholipids, and triglycerides.

In contrast to HDL, low density lipoproteins (LDL), which generally have a density of approximately 1.019–1.063 g/ml contain Apo B-100 in association with various lipids. In particular, the amounts of the lipids, cholesterol and cholesteryl esters are considerably higher in LDL than in HDL, when measured as a percentage of dry mass LDL are particularly important in delivering cholesterol to peripheral tissues.

Very low density lipoproteins (VLDL) have a density of approximately 0.95–1.006 g/ml and also differ in composition from other classes of lipoproteins both in their protein and lipid content. VLDL generally have a much higher amount of triglycerides than do HDL or LDL and are particularly important in delivering endogenously synthesized triglycerides from liver to adipose and other tissues. The features and functions of various lipoproteins have been reviewed (see, for example, Mathews, C. K. and van Holde, K. E., *Biochemistry*, pp. 574–576, 626–630 (The Benjamin/Cummings Publishing Co., Redwood City, Calif., 1990); Havel, R. J., et al., et al., "Introduction: Structure and metabolism of plasma lipoproteins", In *The Metabolic Basis of Inherited Disease, 6th ed.*, pp. 1129–1138 (Scriver, C. R., et al., eds.) (McGraw-Hill, Inc., New York, 1989); Zannis, V. I., et al., "Genetic mutations affecting human lipoproteins, their receptors, and their enzymes", In *Advances in Human Genetics*, Vol. 21, pp. 145–319 (Plenum Press, New York, 1993)).

Decreased susceptibility to cardiovascular disease, such as atherosclerosis, is generally correlated with increased absolute levels of circulating HDL and also increased levels of HDL relative to circulating levels of lower density lipoproteins such as VLDL and LDL (see, e.g., Gordon, D. J., et al., *N. Engl. J. Med.,* 321: 1311–1316 (1989); Castelli, W. P., et al., *J. Am. Med. Assoc.,* 256: 2835–2838 (1986); Miller, N. E., et al., *Am. Heart J.,* 113: 589–597 (1987); Tall, A. R., *J. Clin. Invest.,* 89: 379–384 (1990); Tall, A. R., *J. Internal Med.,* 237: 5–12 (1995)).

Cholesteryl ester transport protein (CETP) mediates the transfer of cholesteryl esters from HDL to TG-rich lipoproteins such as VLDL and LDL, and also the reciprocal exchange of TG from VLDL to HDL (Tall, A. R., *J. Internal Med.,* 237: 5–12 (1995); Tall, A. R., *J. Lipid Res.,* 34: 1255–1274 (1993); Hesler, C. B., et al., *J. Biol. Chem.,* 262: 2275–2282 (1987); Quig, D. W. et al., *Ann. Rev. Nutr.,* 10: 169–193 (1990)). CETP may play a role in modulating the levels of cholesteryl esters and triglyceride associated with various classes of lipoproteins. A high CETP cholesteryl ester transfer activity has been correlated with increased levels of LDL-associated cholesterol and VLDL-associated cholesterol, which in turn are correlated with increased risk of cardiovascular disease (see, e.g., Tato, F., et al., *Arterioscler. Thromb. Vascular Biol.,* 15: 112–120 (1995)).

Hereinafter, LDL-C will be used to refer to total cholesterol including cholesteryl esters and/or unesterified cholesterol associated with low density lipoprotein. VLDL-C will be used to refer to total cholesterol including cholesteryl esters and/or unesterified cholesterol associated with very low density lipoprotein. HDL-C will be used to refer to total cholesterol including cholesteryl esters and/or unesterified cholesterol associated with high density lipoprotein.

CETP isolated from human plasma is a hydrophobic glycoprotein having 476 amino acids and a molecular weight of approximately 66,000 to 74,000 daltons on sodium dodecyl sulfate (SDS)-polyacrylamide gels (Albers. J. J., et al., *Arteriosclerosis,* 4: 49–58 (1984); Hesler, C. B., et al., *J. Biol. Chem.,* 262: 2275–2282 (1987); Jarnagin, S. S., et al., *Proc. Natl. Acad. Sci. USA,* 84: 1854–1857 (1987)). A cDNA encoding human CETP has been cloned and sequenced (Drayna, D., et al., *Nature,* 327: 632–634 (1987)). Polymorphism in human CETP has recently been reported and may be associated with disease in lipid metabolism (Fumeron et al., *J. Clin. Invest.,* 96: 1664–1671 (1995); Juvonen et al.,*J. Lipid Res.,* 36: 804–812 (1995)). CETP has been shown to bind CE, TG, phospholipids (Barter, P. J. et al., *J. Lipid Res.,* 21:238–249 (1980)), and lipoproteins (see, e.g., Swenson, T. L., et al., *J. Biol. Chem.,* 264: 14318–14326 (1989)). More recently, the region of CETP defined by the carboxyl terminal 26 amino acids, and in particular amino acids 470 to 475, has been shown to be especially important for neutral lipid binding involved in neutral lipid transfer (Hesler, C. B., et al., *J. Biol. Chem.,* 263: 5020–5023 (1988)), but not phospholipid binding (see, Wang, S., et al., *J. Biol. Chem.,* 267: 17487–17490 (1992); Wang, S., et al., *J. Biol. Chem.,* 270: 612–618 (1995)).

A monoclonal antibody (Mab), TP2 (formerly designated 5C7 in the literature), has been produced which inhibits completely the cholesteryl ester and triglyceride transfer activity of CETP, and to a lesser extent the phospholipid transfer activity (Hesler, C. B., et al., *J. Biol. Chem.,* 263: 5020–5023 (1988)). The epitope of TP2 was localized to the carboxyl terminal 26 amino acids, i.e., the amino acids from arginine-451 to serine-476, of the 74,000 dalton human CETP molecule (see, Hesler, C. B., et al., (1988)). TP2 was reported to inhibit both human and rabbit CETP activity in vitro and rabbit CETP in vivo (Yen, F. T., et al., *J. Clin. Invest.,* 83: 2018–2024 (1989) (TP2 reacting with human CETP); Whitlock et al., *J. Clin. Invest.*, 84: 129–137 (1989) (TP2 reacting with rabbit CETP)). Further analysis of the region of CETP bound by TP2 revealed that amino acids between phenylalanine-463 and leucine-475 are necessary for TP2 binding and for neutral lipid (e.g., cholesteryl ester) transfer activity (see, Wang, S., et al., 1992).

A number of in vivo studies utilizing animal models or humans have indicated that CETP activity can affect the level of circulating cholesterol-containing HDL. Increased CETP cholesteryl ester transfer activity can produce a decrease in HDL-C levels relative to LDL-C and/or VLDL-C levels which in turn is correlated with an increased susceptibility to atherosclerosis. Injection of partially purified human CETP into rats (which normally lack CETP activity), resulted in a shift of cholesteryl ester from HDL to VLDL, consistent with CETP-promoted transfer of cholesteryl ester from HDL to VLDL (Ha, Y. C., et al., *Biochim. Biophys. Acta*, 833: 203–211 (1985); Ha, Y. C., et al., *Comp. Biochem. Physiol.*, 83B: 463–466 (1986); Gavish, D., et al., *J. Lipid Res.*, 28: 257–267 (1987)). Transgenic mice expressing human CETP were reported to exhibit a significant decrease in the level of cholesterol associated with HDL (see, e.g., Hayek, T., et al., *J. Clin. Invest.*, 90: 505–510 (1992); Breslow, J. L., et al., *Proc. Natl. Acad. Sci. USA*, 90: 8314–8318 (1993)). Furthermore, whereas wild-type mice are normally highly resistant to atherosclerosis (Breslow, J. L., et al., *Proc. Natl. Acad. Sci. USA*, 90: 8314–8318 (1993)), transgenic mice expressing a simian CETP were reported to have an altered distribution of cholesterol associated with lipoproteins, namely, elevated levels of LDL-C and VLDL-C and decreased levels of HDL-C (Marotti K. R., et al., *Nature*, 364: 73–75 (1993)). Transgenic mice expressing simian CETP also were more susceptible to dietary-induced severe atherosclerosis compared to non-expressing control mice and developed atherosclerotic lesions in their aortas significantly larger in area than those found in the control animals and having a large, focal appearance more typical of those found in atherosclerotic lesions in humans (Marotti et al., id). Intravenous infusion of anti-human CETP monoclonal antibodies (Mab) into hamsters and rabbits inhibited CETP activity in vivo and resulted in significantly increased levels of HDL-C levels, decreased levels of HDL-triglyceride, and increased HDL size; again implicating a critical role for CETP in the distribution of cholesterol in circulating lipoproteins (Gaynor, B. J., et al., *Atherosclerosis*, 110: 101–109 (1994) (hamsters); Whitlock, M. E., et al., *J. Clin. Invest.*, 84: 129–137 (1989) (rabbits)).

CETP deficiency has also been studied in humans. For example, in certain familial studies in Japan, siblings that were homozygous for non-functional alleles of the CETP gene had no detectable CETP activity. Virtually no atherosclerotic plaques were exhibited by these individuals, who also showed a trend toward longevity in their families (see, e.g., Brown, M. L., et al., *Nature*, 342: 448–451 (1989); Inazu, A., et al., *N. Engl. J. Med.*, 323: 1234–1238 (1990); Bisgaier, C. L., et al., *J. Lipid Res.*, 32: 21–23 (1991)). Such homozygous CETP-deficient individuals also were shown to have an anti-atherogenic lipoprotein profile as evidenced by elevated levels of circulating HDL rich in cholesteryl ester, as well as overall elevated levels of HDL, and exceptionally large HDL, i.e., up to four to six times the size of normal HDL (Brown, M. L., et al., 1989, p. 451). The frequency of this mutation in Japan is relatively high, and may account for an elevated level of HDL in a significant fraction of the Japanese population.

The above studies indicate that CETP plays a major role in transferring cholesteryl ester from HDL to VLDL and LDL, and thereby in altering the relative profile of circulating lipoproteins to one which is associated with an increased risk of cardiovascular disease (e.g., decreased levels of HDL-C and increased levels of VLDL-C and LDL-C). Marotti et al. (above) interpreted their data as indicating that a CETP-induced alteration in cholesterol distribution was the principal reason that arterial lesions developed more rapidly in transgenic, CETP-expressing mice than in non-transgenic control mice when both groups were fed an atherogenic diet. Taken together, the current evidence suggests that increased levels of CETP activity may be predictive of increased risk of cardiovascular disease. Modulation or inhibition of endogenous CETP activity is thus an attractive therapeutic method for modulating the relative levels of lipoproteins to reduce or prevent the progression of or to induce regression of cardiovascular diseases, such as atherosclerosis.

It would be advantageous, therefore, to discover compounds and methods to control CETP activity which would be helpful in preventing or treating cardiovascular disease. To be an effective pharmacological therapeutic, a compound when administered to a significant majority of recipients, ideally, would not elicit an immune response which neutralizes the beneficial activity or effect of the therapeutic compound, must not promote a hypersensitive state in the individual receiving the therapeutic compound, and must not produce untoward side effects. It would also be advantageous if such compounds and methods avoided the necessity for continuous or frequently repeated treatments.

SUMMARY OF THE INVENTION

This invention provides compounds and methods useful for the modulation or inhibition of cholesteryl ester transfer protein (CETP) activity. In particular, vaccine peptides are described which, when administered to a mammal raise an antibody response against the mammal's own endogenous CETP thereby promoting a prophylactic or therapeutic effect against cardiovascular disease, such as atherosclerosis. Such vaccine peptides comprise a helper T cell epitope portion comprising a "universal" or "broad range" immunogenic helper T cell epitope, linked, preferably covalently, to a B cell epitope portion comprising one or more B cell epitopes from CETP, such as found in the carboxyl terminal portion of human CETP protein that is involved in a neutral lipid binding or a transfer activity of CETP. Other B cell epitopes from CETP may also be used. Preferably, the B cell epitopes from CETP used in the B cell epitope portion of the vaccine peptides of this invention induce antibodies to endogenous CETP (autoreactive antibodies) which either block CETP function or lead to clearance of circulating CETP in the blood. In addition, the B cell epitopes used in the vaccine peptides of this invention preferably do not also comprise a T cell epitope of CETP so that the possibility of T cell-mediated autoimmune liver damage is avoided.

The vaccine peptides of this invention include various "multivalent" embodiments. For example, multivalent peptides present the immune system with more than a single universal or broad range helper T cell or B cell epitope. Such multivalent vaccine peptides include those which have multiple (two or more) copies of the same or different universal or broad range immunogenic helper T cell epitope and/or multiple copies of the same or different B cell epitope from the CETP protein. Those peptides having more than one unique B cell epitope to which different antibodies can bind may promote the formation of immune complexes to effectively clear CETP from the circulatory system.

In a preferred embodiment, the helper T cell epitope portion of a vaccine peptide of this invention is derived from an amino acid sequence of a universally (broad range) immunogenic helper T cell epitope, such as those found in tetanus and diptheria toxoids, or in antigenic peptides known from pertussis vaccine, Bacile Calmette-Guerin (BCG), polio vaccine, measles vaccine, mumps vaccine, rubella vaccine, purified protein derivative (PPD) of tuberculin, *Mycobacterium tuberculosis* hsp-70, and keyhole limpet hemocyanin. Furthermore, various universal (or broad range) antigenic helper T cell epitopes may be linked to one another to form multiple (i.e., multivalent) universal antigenic helper T cell epitope portions of the vaccine peptides of this invention.

In a more preferred embodiment of a vaccine peptide of this invention, an amino terminal cysteine residue is covalently linked to an amino acid sequence of a broad range or universal antigenic helper T cell epitope of tetanus toxoid forming the sequence C Q Y I K A N S K F I G I T E (amino acids 1 to 15 of SEQ ID NO:2), which is covalently linked to a B cell epitope portion of a vaccine peptide having the carboxyl terminal CETP amino acid sequence F G F P E H L L V D F L Q S L S (amino acids 16 to 31 of SEQ ID NO:2).

In another preferred embodiment, a multivalent vaccine peptide comprises an amino acid sequence of a broad range or universal antigenic helper T cell epitope of tetanus toxoid, which in turn is covalently linked to a B cell epitope portion consisting of two B cell epitopes of CETP. In one such preferred embodiment of this invention, the multivalent vaccine peptide has the amino acid sequence of SEQ ID NO:8: C Q Y I K A N S K F I G I T E L F P R P D Q Q H S V A Y T F E E D I F G F P E H L L V D F L Q S L S in which an amino terminal cysteine is linked to a T cell epitope from tetanus toxoid (amino acids 2 to 15 of SEQ ID NO:8) linked to an amino acid sequence containing two B cell epitopes of human CETP, i.e., amino acids 349 to 367 and amino acids 461 to 476 of the amino acid sequence for mature human CETP (SEQ ID NO:4). In still another preferred embodiment of this invention, a multivalent vaccine peptide of this invention contains B cell epitopes from the homologous regions of the rabbit CETP (i.e., amino acids 350 to 368 and 481 to 496 of SEQ ID NO:6) and has the amino acid sequence of SEQ ID NO:9: M Q Y I K A N S K F I G I T E R F P R P D G R E A V A Y R F E E D I F G F P K H L L V D F L Q S L S, in which an amino terminal methionine is linked to a T cell epitope from tetanus toxoid (amino acids 2 to 15 of SEQ ID NO:8) which is linked to an amino acid sequence containing the two B cell epitopes from rabbit CETP.

The peptides of this invention may also be linked to one another via a bifunctional linker molecule or a peptide linker molecule having minimal or no immunogenicity. In addition, the peptides may be linked to a common molecule to form peptide assemblies in which multiple copies of the peptides are arranged close to one another. Such multicopy (multivalent) peptide assemblies may be more immunogenic, that is, produce a more effective immune response to endogenous CETP than vaccines comprising unassociated individual peptides.

The vaccine compounds of this invention also may be used in combination with a pharmaceutically acceptable adjuvant.

The immunogenic vaccine peptides of this invention elicit the production of antibodies that are reactive with or recognize endogenous CETP. Administration of vaccine peptides to test animals resulted in a decline in the relative levels of total cholesterol and HDL-C and resulted in a decrease in the development of atherosclerotic lesions. The elicited endogenous anti-CETP antibodies thus promote a physiological condition correlated with decreased risk of cardiovascular disease, and they appear to have a direct effect on preventing or decreasing the formation of atherosclerosis plaques.

DETAILED DESCRIPTION OF THE INVENTION

Figure 1:
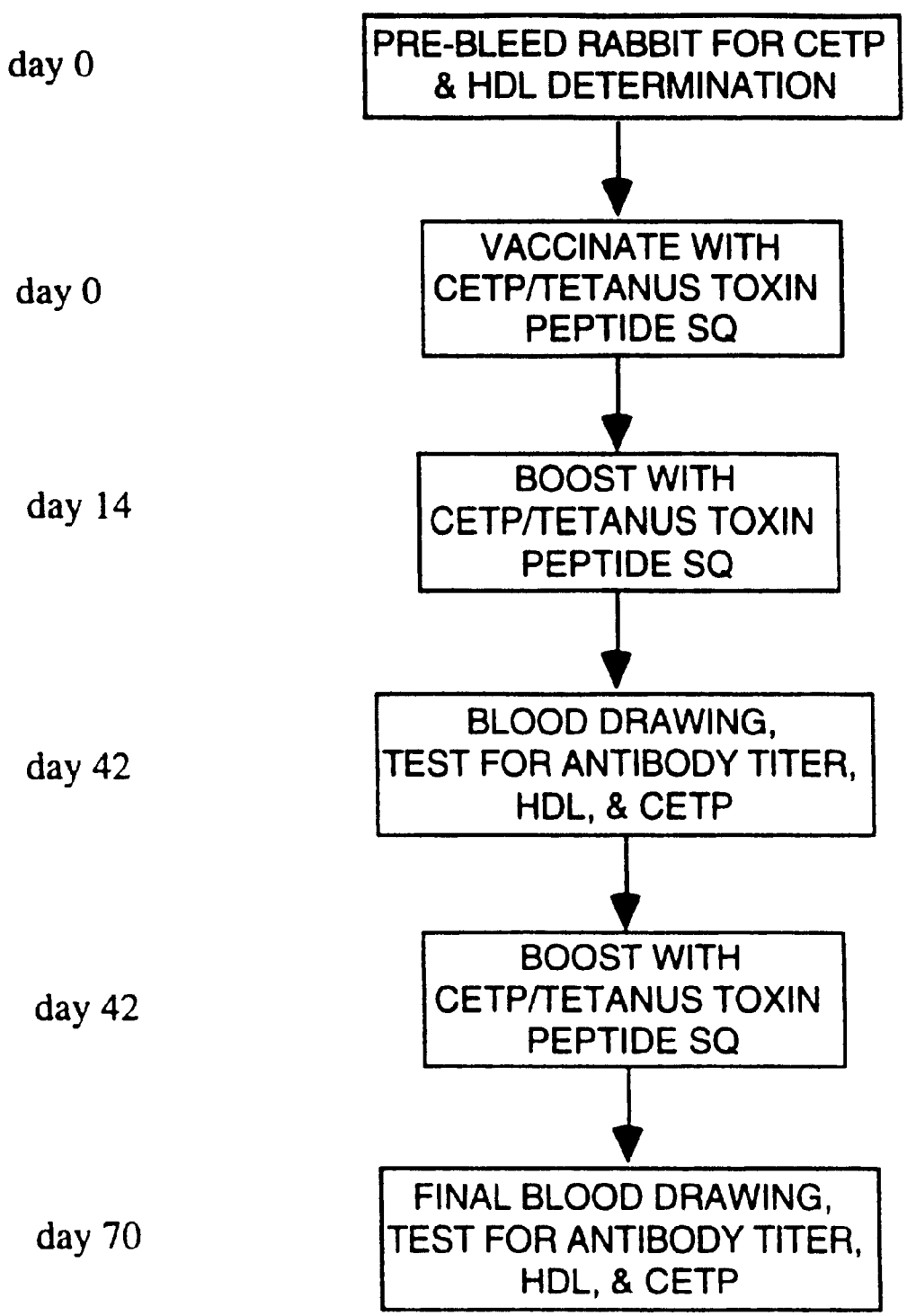
FIG. 1. Flow chart of the protocol for admiration of a vaccine peptide to (vaccination of) rabbits and for withdrawing blood samples for analysis of vaccine efficacy. A control rabbit received no vaccine peptide.

As noted above, a decreased risk of atherosclerosis has been correlated with relatively low circulating levels of LDL and VLDL and relatively high levels of HDL. The levels of such circulating lipoproteins are directly influenced, at least in part, by the endogenous levels of CETP activity. In particular, high CETP activity promotes transfer of neutral lipids, such as cholesteryl esters from HDL to VLDL and LDL. Accordingly, CETP is a relatively precise target in humans and other animals for altering the relative levels of LDL, VLDL and HDL in the circulatory system (see, e.g., Tato, F., et al., *Arteriosclero. Thromb. Vascular Biol.*, 15: 112–120 (1995); Tall, A. R., *J. Internal Med.*, 237: 5–12 (1995)). This invention is directed to the control of endogenous CETP activity. by providing CETP vaccine peptides useful for promoting an immune response in individuals against their endogenous CETP, thereby promoting a physiological condition e.g., increased level of HDL or decreased level of LDL, correlated with a decreased risk of atherosclerosis. In addition, promoting an immune response against endogenous CETP using the vaccine peptides of this invention can provide, prevent, or inhibit the progression of lesions in tissue susceptible to atherosclerosis.

1. Peptides and Compositions for Modulation of CETP Activity

As used herein, a CETP vaccine peptide is a peptide comprising a helper T cell epitope portion comprising an amino acid sequence of a universal (i.e., broad range) antigenic helper T cell epitope and a B cell epitope portion comprising an amino acid sequence of a B cell epitope of CETP, such as the carboxyl terminal region of CETP involved in neutral lipid binding and/or neutral lipid transfer activity. Such CETP vaccine peptides are antigenic, that is, they elicit production of specific antibodies for that peptide which bind endogenous CETP. Thus, the CETP vaccine peptides of this invention are immunogenic moieties that have the capacity to stimulate the formation of antibodies which specifically bind endogenous CETP and/or inhibit endogenous CETP activity.

A. Helper T Cell Epitope Portion of Vaccine Peptides

Peptides useful in the compositions and methods of this invention comprise a helper T cell epitope portion and a B cell epitope portion. The helper T cell epitope portion (or simply, "T cell epitope portion") has an amino acid sequence derived from at least one universal antigenic (or universal immunogenic or broad range) helper T cell epitope (also called an immunogenic carrier peptide), which is defined as a peptide, or derivative thereof which can be presented by multiple major histocompatibility complex (MHC) haplotypes and thereby activate helper T cells, which in turn, stimulate B cell growth and differentiation. As discussed further below, the B cell epitope portion (also called a CETP-related peptide portion) of the vaccine peptides described herein has an amino acid sequence comprising a B cell epitope of the CETP protein, such as a portion of the carboxyl terminal region of the enzyme CETP that is involved in neutral lipid binding and/or neutral lipid transfer.

Examples of what are termed "universal" or "broad range" antigenic helper T cell epitopes which have been used as immunogenic carrier peptides for human vaccination are known in the art. These include, for example, epitopes of tetanus toxoid (tt) and diptheria toxoid (dt) (see, e.g., Panina-Bordignon, P., et al., *Eur. J. Immunol*, 19: 2237–2242 (1989) (characterization of universal tetanus toxoid helper T cell epitope peptides); Etlinger, H., *Immunol. Today*, 13: 52–55 (1992); Valmori, D., et al., *J. Immunol.*, 149: 717–721 (1992) (use of universal tt epitopes in candidate antimalarial vaccine); Talwar, G. P., et al., *Proc. Natl. Acad. Sci. USA*, 91: 8532–8536 (1994) (use of tt and dt as universal epitopes in anti-human chorionic gonadotropin vaccine); Talwar, G. P., et al., *Proc. Natl. Acad. Sci. USA*, 91: 8532–8536 (1994)). In addition to tt and dt, other helper T cell epitope sequences useful in this invention include those derived from antigenic peptides known from pertussis vaccine, Bacile Calmette-Guerin (BCG), polio vaccine, measles vaccine, mumps vaccine, rubella vaccine, and purified protein derivative (PPD) of tuberculin (see, e.g., Etlinger, H., *Immunol. Today*, 13: 52–55 (1992)); incorporated herein by reference). Furthermore, two or more copies of the same or various different universal antigenic helper T cell epitopes may be linked to one another to form multiple or multivalent helper T cell epitope portions of the vaccine peptides of this invention. For example, a vaccine peptide of this invention can be synthesized containing a multiple or multivalent helper T cell epitope portion comprising an amino acid sequence of a tt helper T cell epitope and a dt helper T cell epitope.

In addition, immunogenicity of a vaccine peptide of this invention may be further enhanced by linking the helper T cell epitope portion to a peptide sequence of a xenogeneic CETP or a related protein homologous to CETP. Such an approach was used previously in a human vaccine to human chorionic gonadotropin (see, Talwar, G. P., et al., *Proc. Natl. Acad. Sci. USA.*, 91: 8532–8536 (1994)); heterospecies dimer formed between an amino acid sequence from β subunit of human chorionic gonadotropin and an amino acid sequence of α subunit of ovine luteinizing hormone). Examples of proteins related to CETP that might be used in this approach include, for example, phospholipid transfer protein and neutrophil bactericidal protein (see, Day, J. R., et al., *J. Biol. Chem.*, 269: 9388–91 (1994); Gray, P. W., et al., *J. Biol. Chem.*, 264: 9505–9509 (1989)).

Other immunogenic carrier molecules such as keyhole limpet hemocyanin (KLH) may also be used alone or in combination with other universal antigenic helper T cell epitopes. For example, KLH contains multiple lysine residues in its amino acid sequence. Each of these lysines is a potential site at which a vaccine peptide described herein could be linked (for example, maleimide-activated KLH, Catalog No. 77106, Pierce, Rockford, Ill.). Such an arrangement is a vaccine peptide assembly that is extensively multivalent for both helper T cell epitopes (i.e., those helper T cell epitopes of the KLH amino acid sequence in combination with those helper T cell epitopes of the multiple copies of the attached vaccine peptides) and B cell epitopes of CETP (i.e., those B cell epitopes of CETP in the multiple copies of the vaccine peptides attached to the KLH amino acid sequence).

Recently, another immunogenic carrier molecule, hsp70 from *Mycobacterium tuberculosis*, has been shown to be an especially potent antigen containing multiple B and T cell epitopes (Suzue and Young, *J. Immunol.*, 156: 873–879 (1996)). The hsp70 protein can be linked by standard cross-linking agents to vaccine peptides of this invention to enhance immunogenicity. Alternatively, nucleic acid molecules coding for vaccine peptides of this invention can be inserted into an expression vector which permits the expression of a recombinant protein consisting of the vaccine peptide fused to the amino terminus of hsp70.

Preferably, the helper T cell epitope portion of the vaccine peptides of this invention comprises a universal antigenic tt or dt helper T cell epitope. In a more preferred embodiment, the peptides of this application use universal antigenic tt helper T cell epitopes having amino acid sequences Q Y I K A N S K F I G I T E (amino acids 2 to 15 of SEQ ID NO:2) and F N N F T V S F W L R V P K V S A S H L E (SEQ ID NO:3). Most preferably, the peptides of this invention use the universal antigenic tt helper T cell epitope having the amino acid sequence Q Y I K A N S K F I G I T E (amino acids 2 to 15 of SEQ ID NO:2).

In addition to the various examples of helper T cell epitopes discussed above, whether another peptide or protein is useful as a helper T cell epitope for the T cell epitope portion of the vaccine peptides of this invention can be determined using a standard proliferation assay for class II (helper) T cell epitopes (see, for example, pages 3.12.9–3.12.14, In *Current Protocols in Immunology, Vol.* 1 (Coligan et al., eds.) (John Wiley & Sons, Inc., New York, N.Y., 1994)).

B. B Cell Epitope (CETP-Related) Portion of Vaccine Peptides

The B cell epitope portion of the vaccine peptides described herein comprise one or more B cell epitopes of the CETP protein endogenous to the vaccinated mammal, or one or more B cell epitopes of a CETP different from the endogenous CETP but which is immunologically (antibody) cross reactive with the endogenous CETP.

The B cell epitope portion of the vaccine peptides of this invention may comprise one or more B cell epitopes of the endogenous CETP of the individual to be vaccinated for raising antibodies that inhibit the endogenous CETP activity. However, it is also within the scope of this invention that the B cell epitope portion of the vaccine peptides of this invention comprise B cell epitopes of CETP molecules that are similar, but not identical to the endogenous CETP of the individual to be vaccinated. Certain B cell epitopes of such similar, but non-identical CETP proteins may contain epitopes which enhance the immune response in the vaccinated individual. Generally, CETP molecules which have amino acid sequences that are at least approximately 80 percent homologous to the endogenous CETP may be used as a source of B cell epitopes in the B cell epitope portion of the vaccine peptides of this invention. As an example, the rabbit and human CETP proteins have an amino acid sequence homology of approximately 80 percent. The mature rabbit CETP has the amino acid sequence of SEQ ID NO:6 and the mature human CETP from liver has the amino acid sequence of SEQ ID NO:4. Accordingly, in an example of such an embodiment of the vaccine peptides of this invention, the B cell epitope portion comprises one or more B cell epitopes of a rabbit and/or a human CETP, and such a vaccine peptide may be used in either rabbits or humans to inhibit the endogenous CETP activity.

In addition, the B cell epitope portion of the vaccine peptides of this invention comprises a portion of the amino acid sequence of the mature CETP protein (SEQ ID NO: 4) consisting of at least 6 amino acid sequences in length and which does not significantly, if at all, stimulate T cell proliferation in vitro.

In a preferred embodiment, the vaccine peptides of this invention have multivalent B cell epitope portions of vaccine peptides of this invention which comprise two or more different B cell epitopes of CETP. Such multivalent helper T cell epitope portions are especially preferred because they present multiple target sites at which elicited antibodies can bind to the endogenous CETP thereby promoting more extensive immune complex formation and/or the likelihood of inhibiting CETP cholesteryl transfer activity.

In addition, it is preferred that a B cell epitope portion of the vaccine peptides should not comprise a B cell epitope which also comprises a T cell epitope that can be presented by endogenous MHC class I molecules. Such T cell epitopes of CETP could be presented on the surface of hepatocytes in the context of MHC class I and elicit a cytotoxic T cell response and thereby damage liver tissue. Whether a particular CETP B cell epitope comprises a class I T cell epitope can be determined using a standard cytotoxic T cell assay (see, for example, pages 3.11.4–3.11.7, In *Current Protocols in Immunology, Vol.* 1 (John Wiley & Sons, Inc., New York, N.Y., 1994)).

In another embodiment, the B cell epitope portion of the vaccine peptides of this invention comprises the carboxyl terminal 26 amino acids of human CETP (see SEQ ID NO: 1) or fragments thereof that retain a conformation or an activity of the carboxyl terminal 26 amino acid region of CETP, e.g., fragments of the CETP carboxyl terminus which are at least six consecutive amino acids in length and which are involved in specific neutral lipid binding and/or specific neutral lipid transfer activity of CETP. More preferably, the B cell epitope (or CETP-related) portion of the vaccine peptides of this invention comprises any fragment of the carboxyl terminal region of CETP which is at least eleven consecutive amino acids in length, which retains the conformation of the carboxyl terminal 26 amino acid region of CETP, which is involved in the neutral lipid binding and/or transfer activity of CETP, and which is accessible to antibody binding (see, e.g., Wang, S., et al., *J. Biol. Chem.,* 267: 17487–17490 (1992); Wang, S., et al., *J. Biol. Chem.,* 268: 1955–1959 (1993)). In addition, several Mabs have been generated to this region, including the Mab TP2, that block function of human CETP and also rabbit CETP, implying that this epitope is conserved by human and rabbit CETP proteins (Whitlock et al., *J. Clin. Invest.,* 84: 129–137 (1989). This is confirmed by the fact that the carboxyl terminal 22 amino acids of human and rabbit CETP differ at only one position, i.e., the glutamic acid residue at position 465 in the amino acid sequence of human CETP in SEQ ID NO: 4 is replaced with a lysine at the homologous position (position 485) in the rabbit sequence (SEQ ID NO:6; see also, Nagashima et al., *J. Lipid Res.,* 29: 1643–1649 (1988)).

Alternatively, the B cell epitope portion comprises a derivative of the carboxyl terminal 26 amino acid region of CETP containing amino acid changes (deletions, additions or substitutions) that do not significantly alter or destroy the neutral lipid binding or transfer activity of CETP (see, Wang et al., id., (1992); Wang et al., id., (1993)). Such changes in the amino acid sequence of a targeted endogenous CETP include, but are not limited to, what are generally known as conservative amino acid substitutions, such as substituting an amino acid of the CETP sequence with another of similar structure, charge, or hydrophobicity. Any addition or substitution to the CETP sequence that maintains neutral lipid binding and/or transfer activity, but improves stability in vivo or in situ, improves purification, or provides cross-linking sites (e.g., via cysteine-cysteine disulfide bond formation) is also useful in the design of a vaccine peptide of this invention.

Because CETP-mediated transfer of neutral lipids necessarily requires binding of the neutral lipid (e.g., triglycerides, cholesteryl ester), portions of the amino acid sequence of CETP that are involved in neutral lipid binding are also useful in designing the vaccine peptides of this invention. Some portions of the amino acid sequence of CETP used to design the vaccine peptides of this invention may be involved in both neutral lipid binding as well as the actual catalytic neutral lipid transfer site of CETP. Recent evidence suggests that CETP contains separate binding sites for cholesteryl ester and triglycerides (Melchior, G. W., et al., *J. Biol. Chem.*, 270: 21068–21074 (1995)). Accordingly, incorporating the amino acid sequence for a specific lipid binding site into a vaccine peptide may provide a means to modulate CETP interactions with that specific lipid thereby promoting an anti-atherogenic profile even though the elicited antibodies to CETP do not promote clearance (reduce serum half-life) of circulating CETP. For instance, to modulate triglyceride content of HDL specifically, a B cell epitope derived from the triglyceride binding region of CETP could be incorporated into the B cell epitope portion of a vaccine peptide of this invention. Similarly, to modulate cholesteryl ester content of HDL specifically, a B cell epitope derived from the cholesteryl ester binding region of CETP could be incorporated into the design of a vaccine peptide of this invention. Such vaccine peptides are thus designed to elicit antibodies which block specific lipid binding sites on CETP and thereby influence the specific lipid transferred between HDL and CETP.

Also useful are amino acid sequences of CETP that are at least six consecutive amino acids in length, a minimal size of an epitope in a protein (see, e.g., Watson et al., *Molecular Biology of the Gene*, 4th edition, page 836 (The Benjamin/Cummings Publishing Co., Inc., Menlo Park, Calif., 1987), and more preferably, that are at least eleven consecutive amino acids in length of the carboxyl terminal 26 amino acid region of CETP encoded by any naturally occurring polymorphisms of the CETP gene.

Figure 8A:
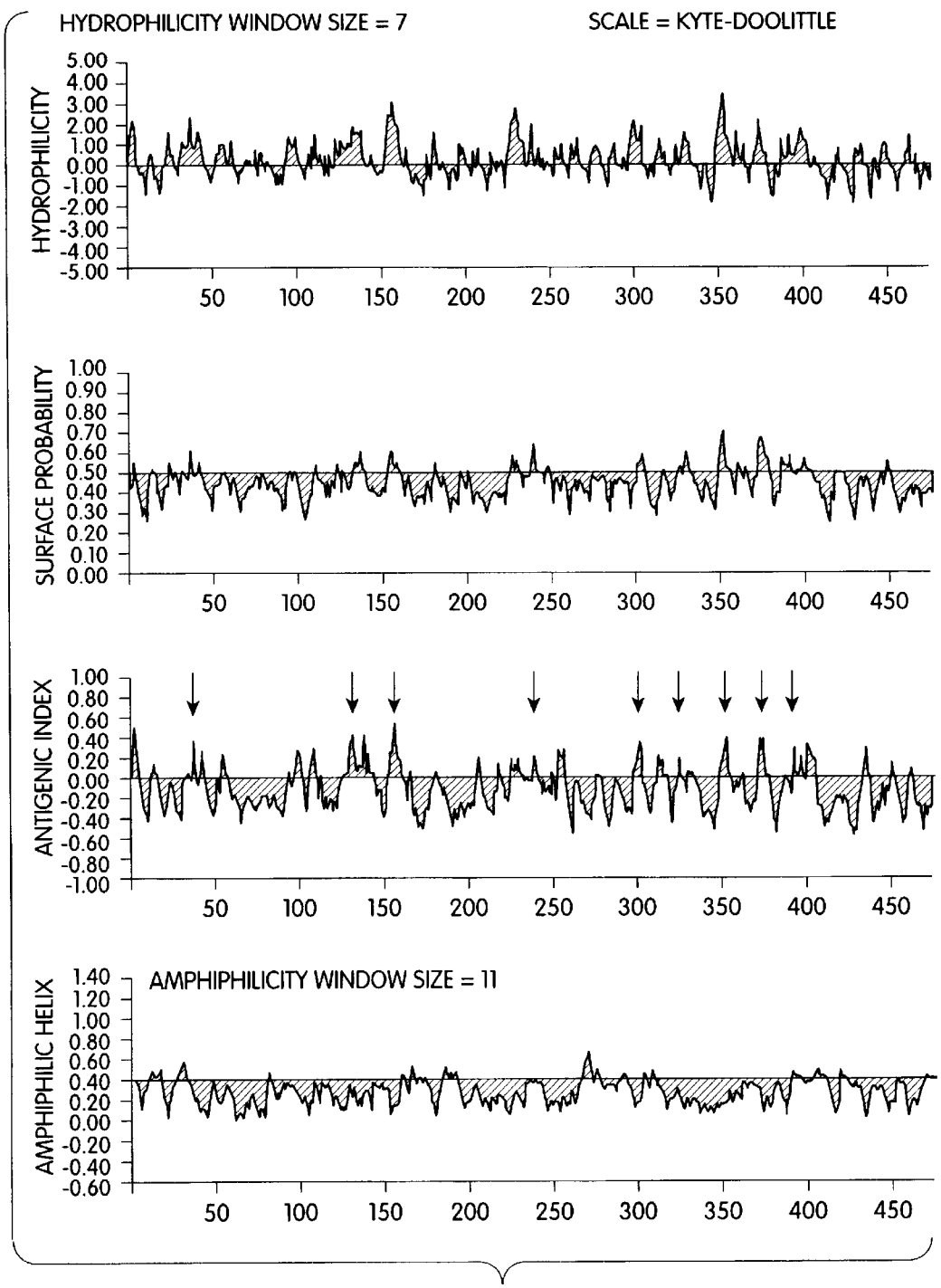
FIGS. 8A and 8B. Typical plots of Hydrophilicity, Surface Probability, Antigenic Index, and Amphilic Helix (FIG. 8A) and Amphiphilic Sheets and Secondary Structure (FIG. 8B) for mature human CETP.
Figure 8B:
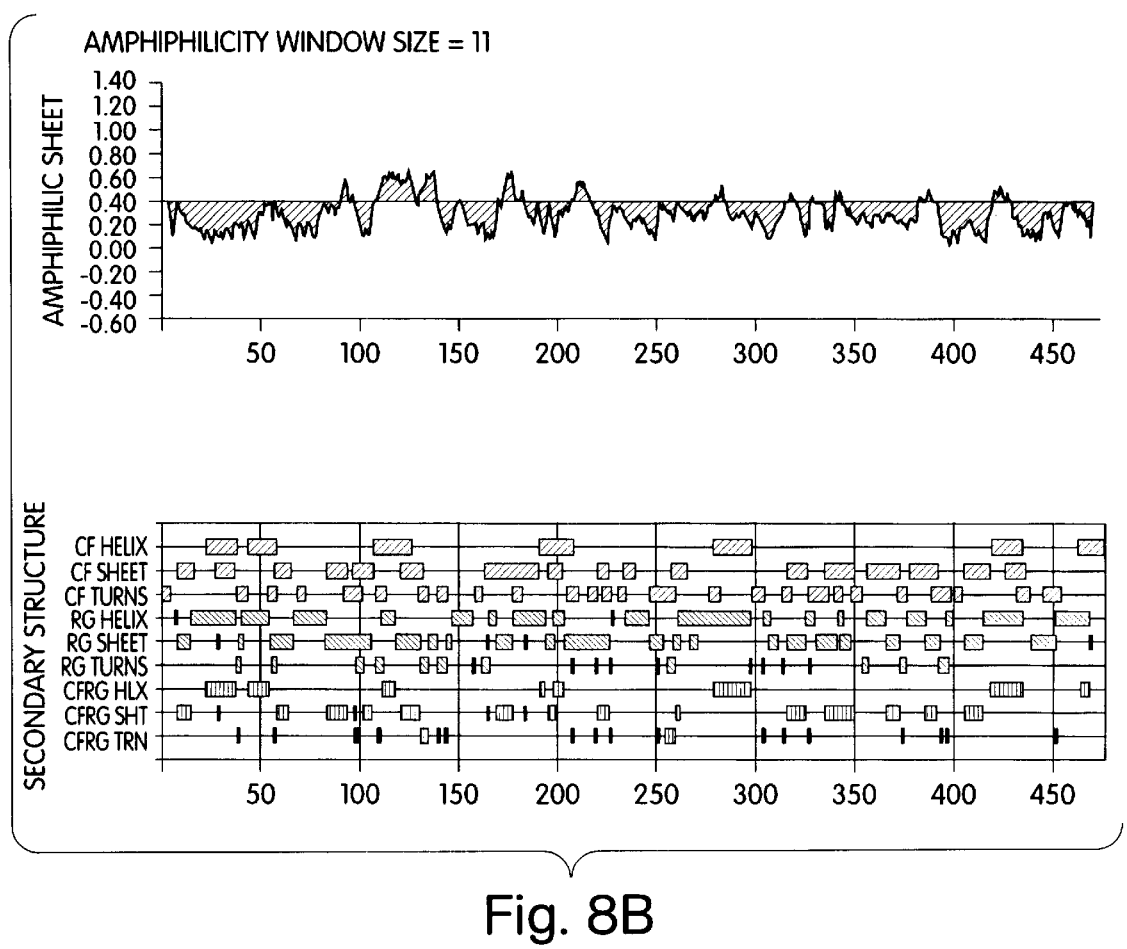

CETP molecules of known amino acid sequence can be analyzed for the location of potential B cell epitopes using algorithms which can identify potential antigenic motifs in the amino acid sequence. For example, by combining analyses of plots of hydrophilicity, surface probability, amphilic helix, amphiphilic sheets and secondary structure (FIGS. 8A and 8B), an Antigenic Index (see FIG. 8A) of the entire protein's amino acid sequence can be derived leading to identification of B cell epitopes potentially useful in the vaccine peptides of this invention.

Methods for testing CETP molecules for neutral lipid binding or their effect on neutral lipid transfer activity are well known in the art, (see, e.g., Swenson, T. L., et al., *J. Biol. Chem.*, 263: 5150–5157 (1988) (assay for lipid binding); Hesler, C. B., et al., *J. Biol. Chem.*, 262: 2275–2282 (1987) (assay for lipid transfer; Bisgaier, C. L., et al., *J. Lipid Res.*, 34: 1625–1634 (1993) (use of fluorescent cholesteryl ester microemulsions in CETP-mediated cholesteryl transfer activity assay); Gaynor, B. J., et al., *Atherosclerosis*, 110: 101–109 (1994) (assay for CETP lipid transfer); Wang et al. (1992) (assaying deletion mutants of CETP for transfer activity); Wang et al., (1993) (assaying single amino acid mutant forms of CETP); incorporated herein by reference). Assays for the transfer activity of CETP are also commercially available (e.g., CETP functional assay by Diagnescent Technologies, Yonkers, N.Y.).

Preferably, the B cell epitope portion of the CETP vaccine peptides of this invention comprises the amino acid sequence L F P R P D Q Q H S V A Y T F E E D I (amino acids 16 to 34 of SEQ ID NO:8) and/or the amino acid sequence F G F P E H L L V D F L Q S L S (amino acids 35 to 50 of SEQ ID NO:8).

C. Production of Vaccine Peptides

The helper T cell epitope and the B cell epitope (CETP-related) portions of the CETP vaccine peptides of this invention are linked together to form immunogenic moieties. The helper T cell epitope and B cell epitope portions may be covalently linked, directly (e.g., via a peptide bond) or via a cross-linking molecule. Where cross-linking molecules are used, they must join the helper T cell epitope and B cell epitope portions of the vaccine peptide together without making the peptide toxic or significantly interfering with or reducing the overall immunogenicity of the vaccine peptide. Suitable cross-linking molecules include amino acids, for example, using one or more glycine residues to form a "glycine bridge" between the helper T cell epitope and B cell epitope portions of the vaccine peptides of this invention. Also contemplated are the formation of disulfide bonds between cysteine residues that have been added to the helper T cell epitope and B cell epitope portions, or the use of cross-linking molecules such as glutaraldehyde (Korn, A. H., et al., *J. Mol. Biol.*, 65: 525–529 (1972)) and EDC (Pierce, Rockford, Ill.) or other bifunctional cross-linker molecules to link a helper T cell epitope portion to a B cell epitope portion. Bifunctional cross-linker molecules possess two distinct reactive sites; one of the reactive sites can be reacted with a functional group on the helper T cell epitope portion to form a covalent linkage and the other reactive site can be reacted with a functional group on a B cell epitope portion to form another covalent linkage, uniting the two portions. General methods for cross-linking molecules are reviewed by Means and Feeney (*Bioconjugate Chem.*, 1: 2–12 (1990)).

Homobifunctional cross-linker molecules have two reactive sites which are chemically the same. Examples of homobifunctional cross-linker molecules include glutaraldehyde; N,N'-bis(3-maleimido-propionyl)-2-hydroxy-1,3-propanediol (a sulfhydryl-specific homobifunctional cross-linker); certain N-succinimide esters, such as disuccinimidyl suberate and dithio-bis-(succinimidyl propionate) and their soluble bis-sulfonic acids and salts (e.g., as available from Pierce Chemicals, Rockford, Ill.; Sigma Chemical Co., St. Louis, Mo.). For this embodiment, the relative concentrations of helper T cell epitope and B cell epitope portions should be adjusted to maximize the number of helper T cell epitope and B cell epitope portions that are linked together and to minimize the linking of identical epitope portions to each other (i.e., to avoid, for example, helper T cell epitope-helper T cell epitope or B cell epitope-B cell epitope homodimer formation).

Preferably, the bifunctional cross-linker molecule is a heterobifunctional linker molecule, meaning that the linker molecule has at least two reactive sites that can be separately covalently attached to a T cell epitope and a B cell epitope. Use of such heterobifunctional linker molecules permits chemically separate and stepwise addition (vectorial conjugation) of each of the reactive sites of the linker molecule to the helper T cell and B cell epitope portions of the vaccine peptide. Heterobifunctional cross-linker molecules that may be used to link helper T cell epitope and B cell epitope portions together other include m-maleimidobenzoyl-N-hydroxysuccinimide ester (see, Green, N., et al., *Cell*, 28: 477–487 (1982); Palker et al., *Proc. Natl. Acad. Sci. USA*, 84: 2479–2483 (1987); m-maleimido-benzoylsulfosuccinimide ester; γ-maleimidobutyric acid N-hydroxysuccinimide ester; and N-succinimidyl 3-(2-pyridyl-dithio)propionate (see, Carlsson, J., et al., *Biochem. J.*, 173: 723–737 (1978); Sigma Chemical Co., St. Louis. Mo.).

Furthermore, the helper T cell epitope and B cell epitope portions may be linked to a common carrier molecule, such as serum albumin or a resin or polymeric bead. Linking helper T cell epitope and B cell epitope portions to a common carrier may be accomplished using a cross-linker molecule such as glutaraldehyde or other bifunctional cross-linker molecule (see above). For this embodiment, the relative concentrations of helper T cell epitope portion, B cell epitope portion and the common carrier molecule should be adjusted to maximize the number of helper T cell epitope and B cell epitope portions that are linked to the common carrier and to minimize both the linking of identical molecules to each other (i.e., homodimer formation) and the linking of helper T cell epitope and B cell epitope portions to one another (i.e., heterodimer formation). Linking the helper T cell epitope and B cell epitope portions to another molecule or surface (e.g., the surface of a resin or polymer bead) should not significantly disrupt or reduce the immunogenic characteristics of the universal antigenic helper T cell epitope portion or of the B cell epitope (CETP-related) portion sequences. The net effect of using such bifunctional cross-linker molecules is that multiple copies of helper T cell epitope and B cell epitope portions of a vaccine peptide are bound to a common carrier which may enhance an immune response and the production of antibodies that bind to endogenous CETP.

Multiple antigenic peptide (MAP) arrangements have also been demonstrated to be highly effective antigens and immunogens (see, e.g., Tam, J. P., *Proc. Natl. Acad. Sci. USA*, 85: 5409–5413 (1988); Wang, C. Y., et al., *Science*, 254: 285–288 (1991); Marguerite, M., et al., *Mol. Immunol.*, 29: 793–800 (1992)). Such MAP technology, in which the helper T cell epitope and B cell epitope portions of the vaccine peptides described herein are attached to a common core molecule, provides another way to make multivalent peptide assemblies to elicit antibodies against endogenous CETP.

Preferably, the helper T cell epitope and B cell epitope portions of the vaccine peptides of this invention are covalently linked end-to-end to form a continuous peptide. Most preferably, a selected universal antigenic helper T cell epitope portion forms the amino terminal portion of the vaccine peptide with its carboxyl terminal amino acid residue covalently linked in a peptide bond to the amino terminal amino acid of a selected CETP-related amino acid sequence (B cell epitope portion) of the vaccine peptide. However, the reverse order may also be used, i.e., the CETP-related amino acid sequence (B cell epitope portion) of the vaccine peptides of this invention may be positioned to form the amino terminal region of a vaccine peptide and a universal antigenic helper T cell epitope or immunogenic carrier amino acid sequence may comprise the carboxyl terminal portion of the vaccine peptide.

The vaccine peptides of this invention can be made more immunogenic by covalently linking them to multiple copies of the complement protein C3d (Dempsey et al., *Science*, 271: 348–350 (1996)). Alternatively, the vaccine peptides can be derivatized with carbohydrate structures which activate complement and become covalently linked with C3d (Fearon et al, *Science*, 272: 50–54 (1996)). For example, proteins expressed in certain mutant Chinese hamster ovary host cells can be glycosylated with specific carbohydrate structures (Stanley, *Mol. Cell. Biol.*, 9:377–383 (1989)). Recent evidence demonstrates that C3d promotes the recognition of antigens by the acquired immune system eliciting vigorous immune response (Dempsey et al., 1996).

The peptides of this invention can be produced by any of the available methods known in the art to produce peptides of defined amino acid sequence. For example, automated peptide synthesis is available to those skilled in the art by using automated peptide synthesizers (e.g., Synergy™ Peptide Synthesizer by Applied Biosystems; AMS 422 by Abimed, Langenfeld, Germany). Synthesis of such peptides to order is performed as a commercial service by many commercial peptide synthesizing service companies, e.g., Quality Controlled Biochemicals, Inc., Hopkinton, Mass.); Chiron Mimotopes Peptide Systems (San Diego, Calif.); Bachem Bioscience, Inc. (Philadelphia, Pa.); Severn Biotech Ltd. (Kiddeminster; England).

Alternatively, the peptides of this invention may be produced using synthetic and recombinant nucleic acid technology. For example, one of ordinary skill in the art can design from the known genetic code a 5' to 3' nucleic acid sequence encoding a peptide of this invention. The amino acid sequence for a mature CETP from human liver is known (SEQ ID NO:4), as is its corresponding DNA sequence (SEQ ID NO: 5) (see, Drayna et al., *Nature*, 327: 632–634 (1987)). Furthermore, the amino acid sequences for a variety of broad range or "universal" T cell epitopes are known (see, for example, Panina-Bordignon et al., *Eur. J. Immunol.*, 19: 2232–2242 (1989), Etlinger et al. (1990), Pillai et al., *Infect. Immun.*, 63: 1535–1540 (1995)).

A DNA molecule containing the coding sequences of a helper T cell epitope and one or more selected B cell epitope portions (and any inking peptide, such as polyglycine, or other additional residue(s), such as an amino and/or carboxyl terminal cysteine, if so desired) can readily be synthesized either using an automated DNA synthesizer (e.g., Oligo 1000 DNA Synthesizer. Beckman Corp.) or by contracting with a commercial DNA synthesizing service (e.g., Genset Corp., La Jolla, Calif.). The synthesized DNA molecule can then be inserted into any of a variety of available gene expression systems (e.g., bacterial plasmids; bacteriophage expression vectors, retroviral expression vectors, baculoviral expression vectors), using standard methods available in the an (e.g., Sambrook et al., *Molecular Cloning: A Laboratory Manual, Vols.*, 1–3 (Cold Spring Harbor Laboratory, Cold Spring Harbor, N.Y., 1989)) and/or as directed by the manufacturer of a particular commercially available gene expression system (e.g., pPROEX™-1 bacterial cell expression system; SFV eukaryotic cell expression system; BAC-TO-BAC™ baculovirus expression system; Life Technologies, Inc., Gaithersburg, Md.). The expressed peptide is then isolated from the expression system using standard methods to purify peptides. Purification of the peptides of this invention may be expedited by employing affinity chromatography or immunoprecipitation based on using antibodies to the particular helper T cell epitope or B cell epitope (CETP-related portion) amino acid sequence of a vaccine peptide of this invention. For example, the Mab TP2 binds to the carboxyl terminal 26 amino acids of human CETP, and could be useful in one or more immunoaffinity steps in a purification scheme (Hesler, C. B., et al., *J. Biol. Chem.*, 263: 5020–5023 (1988)).

Of course, if DNA molecules are available encoding each of the T cell and B cell epitopes for a particular vaccine peptide, standard recombinant nucleic acid methodologies, including polymerase chain reaction (PCR), can be employed to produce recombinant nucleic acid molecules encoding the vaccine peptides. Such recombinant nucleic acid molecules can be inserted into any of a variety of expression vectors which can be transfected or transformed into appropriate host cells to express the vaccine peptide in culture (see, e.g., Sambrook et al., *Molecular Cloning: A Laboratory Manual, Vols.* 1–3 (Cold Spring Harbor Laboratory, Cold Spring Harbor, N.Y., 1989)). For example, the DNA sequence encoding the mature human CETP from liver has the nucleotide sequence of SEQ ID NO:5 and the DNA sequence encoding the mature rabbit CETP has the nucleotide sequence of SEQ ID NO:7. Particular sequences encoding various B cell epitopes of each of these CETP proteins can be recombined with nucleotide sequences encoding selected T cell epitope(s) and inserted into an expression vector for expression in an appropriate host cell.

An example of a recombinant plasmid that can be used to produce a vaccine peptide is plasmid pCMV-CETP/TT in which the CMV promoter directs transcription of a sequence encoding a vaccine peptide having the amino acid sequence of SEQ ID NO:9: M Q Y I K A N S K F I G I T E R F P R P D G R E A V A Y R F E E D I F G F P K H L L V D F L Q S L S,
wherein an amino terminal methionine is linked to a tetanus toxoid T cell epitope (amino acids 2 to 15 of SEQ ID NO:2) and two B cell epitopes from rabbit CETP (amino acids 350 to 368 and 481 to 496 of SEQ ID NO:6). Plasmid pCMV-CETP/TT has been deposited with the American Type Culture Collection (ATCC, Rockville, Md.) and assigned Accession No. 98038.

In a preferred embodiment, a peptide of this invention also contains an amino terminal cysteine residue, or other residue, covalently linked to the amino terminal amino acid of the helper T cell epitope portion of the vaccine peptide of this invention for use in tethering or coupling the peptide to itself to form dimers of vaccine peptides or to other molecules, such as carrier or cross-linker molecules. More preferably, the vaccine peptide of this invention has the amino acid sequence C Q Y I K A N S K F I G I T E F G F P E H L L V D F L Q S L S (SEQ ID NO:2). Even more preferred is a vaccine peptide of this invention having at least two B cell epitopes of CETP. An example of such a vaccine peptide has the sequence C Q Y I K A N S K F I G I T E L F P R P D Q Q H S V A Y T F E E D I F G F P E H L L V D F L Q S L S (SEQ ID NO:8).

D. Production of Vaccine

The peptides of this invention are used to make vaccines that elicit production of endogenous antibodies which specifically bind to CETP and/or modulate (i.e., decrease or inhibit) endogenous CETP activity. The anti-CETP vaccines of this invention may contain one or several different peptides of this invention. For example, peptides having different helper T cell epitope portions (e.g., different universal helper T cell epitopes) and/or different B cell epitope portions (e.g., different CETP-related portions of the carboxyl terminal 26 amino acids of CETP) may be combined and administered as a single vaccine composition.

Pharmaceutically acceptable adjuvants, such as alum, may be mixed with vaccine peptides described herein to produce vaccines of this invention. Alum is the single adjuvant currently approved for use in administering vaccines to humans (see, Eldrige, J. H., et al., In *Immunobiology of Proteins and Peptides V: Vaccines: Mechanisms, Design, and Applications*, Atassi M. Z., ed. (Plenum Press, New York, 1989), page 192). Recently, alum was used in combination with a sodium phthalyl derivative of lipopolysaccharide to administer a vaccine shown to be effective against human chorionic gonadotropin to humans (see, Talwar, G. P., et al., *Proc. Natl. Acad. Sci. USA*, 91: 8532–8536 (1994)).

Other conventional adjuvants may be used as they are approved for a particular use. For example, biodegradable microspheres comprised of poly (DL-lactide-co-glycolide) have been studied as adjuvants for oral or parenteral administration of vaccines (Eldridge, J. H., et al., In *Immunobiology of Proteins and Peptides V Vaccines; Mechanisms, Design and Applications*, Atassi M. Z., ed. (Plenum Press, New York, 1989), pp. 191–202).

Other adjuvants have been used for administering vaccines to non-human mammals. For example, Freund's Complete Adjuvant (Sigma Chemical Co., St. Louis, Mo.), Freund's Incomplete Adjuvant (Sigma Chemical Co., St. Louis, Mo.), and the RIBI™ Adjuvant System (RAS; RIBI ImmunoChem Research, Inc., Hamilton, Mont.) are well known adjuvants routinely used to administer antigens to animal other than humans. In addition, adjuvant structures may also be mixed with or, preferably, covalently incorporated into peptides of this invention, for example at the amino or carboxyl terminal amino acid residue of the peptides. Such incorporated adjuvants include lipophilic N-palmitoyl-S-[2,3-bis(palmitoyloxy)-propyl)]-cysteine ("Pam$_3$-Cys-OH") at the amino terminus of the peptides of this invention; amphiphilic, water-soluble lipopeptides such as PaM$_3$-Cys-Ser-Lys$_4$ and Pam$_3$-Cys-Ser-Glu$_4$; glycopeptides such as N-acetyl-glucosaminyl-N-acetylmuramyl-alanyl-D-isoglutamine ("GMDP"), muramyl dipeptides, and alanyl-N-adamantyl-D-glutamine; and polyamide gel-based adjuvants which can easily be attached to peptides during their in vitro chemical synthesis (see, *Synthetic Vaccines*, Nicholson, B. H., ed. (Blackwell Scientific Publications, Cambridge, Mass., 1994), pp. 236–238).

In addition, the vaccine peptides of this invention may be linked to other molecules that may enhance the immunogenicity of the peptides. For example, linking peptides of this invention to a surface of a larger molecule, such as serum albumin, may enhance immunogenicity because the epitopes of the vaccine peptides are presented to the immune system of an individual as adjacent multiple repeated copies (see, e.g., Tam, J. P., *Proc. Natl. Acad. Sci. USA*, 85: 5409–5413 (1988); Wang, C. Y., et al., *Science*, 254: 285–288 (1991); Marguerite, M., et al., *Mol. Immunol.*, 29: 793–800 (1992)). Such "multiple" or "multivalent" arrangements of the vaccine peptides of this invention can be created using cross-linker molecules (see above). For example, as noted above, bifunctional cross-linker molecules possess two reactive sites, one of the sites can attach the linker to a vaccine peptide of this invention and the other site is available to react with a different molecule, e.g., a larger protein like serum albumin or a resin or polymeric bead. Thus, covalent cross-linker molecules may be used to link vaccine peptides to other proteins or substrates to form multicopy arrangements of the peptides (multicopy peptide assemblies).

Linking vaccine peptides of this invention to another molecule or surface should be carried out in a manner that does not significantly disrupt or reduce the immunogenic characteristics of the linked helper T cell epitope and B cell epitope (CETP-related) portions of the vaccine peptides. Preferably, the use of such linker molecules enhances the immunogenicity of the vaccine peptides of this invention as evidenced, for example, by a more rapid rise in anti-CETP antibody titer and/or production of higher affinity anti-CETP antibodies than when individuals are administered vaccine peptides that are not linked. Such cross-linker molecules may also be used to attach a peptide of this invention to an "immunogenic enhancer" molecule such as granulocyte-macrophage colony-stimulating factor (GM-CSF), which was been shown to serve as an effective immunogenic enhancer in generating the production of specific anti-tumor antibodies (e.g., Tao, M. H., et al., *Nature*, 362: 755–758 (1993)). Another such immunogenic enhancer is keyhole limpet hemocyanin (KLH) (see, Ada, G. L., In *Fundamental Immunology, third edition*, W. E. Paul, ed. (Raven Press Ltd., New York, 1993), pp. 1309–1352). As noted above, an example of a multivalent arrangement using KLH is the attachment of vaccine peptides to any of several cysteine residues of KLH molecule via disulfide bond formation.

2. Use of Vaccine Peptides

General methods of administering and testing vaccines are well known to those skilled in the art (see, e.g., Talwar, G. P., et al., *Proc. Natl. Acad. Sci. USA*, 91: 8532–8536 (1994)). The peptides of this invention are specifically designed to be administered, either alone or in association with one or more pharmaceutically acceptable carriers or adjuvants, as a vaccine which will elicit an antibody response against endogenous CETP of the vaccine recipient. In some embodiments of this invention, the vaccine peptides may also be combined and administered with vaccines for other diseases or disorders.

The immune response to endogenous CETP should significantly inhibit CETP activity, alter the serum half-life of CETP, cause clearance CETP through formation of immune complexes, alter the trafficking of HDL-cholesterol, shift the equilibrium of cholesterol content of lipoproteins, alter cholesterol catabolism, and/or reduce development of atherosclerotic lesions. Control of LDL, VLDL and/or HDL levels is an accepted indicator or endpoint in treatment of cardiovascular disease as these levels are correlated with a decreased risk of cardiovascular disease or further progression of such disease (Mader, S. S., In *Human Biology, 4th ed.*, pp. 83, 102 (Wm. C. Brown Publishers, Dubuque, Iowa, 1995)). Accordingly, the desired prophylactic or therapeutic effect according to this invention is evidenced by eliciting antibodies in an individual that bind to CETP and/or inhibit CETP activity, or by a relative decrease in LDL and/or VLDL levels compared to HDL levels as the titer of antibody directed against the endogenous CETP rises, or by an elevation of absolute levels of circulating HDL with the production of anti-CETP antibodies, or by an inhibition or decrease in development of atherosclerotic lesions in cardiovascular tissue.

As demonstrated herein, administration of vaccine peptides in a rabbit model of atherosclerosis led to a significant decrease in the development of atherosclerotic plaques in animals fed a cholesterol supplemented diet. This evidence indicates that vaccination to elicit antibodies to endogenous CETP may be a useful method of treating or preventing atherosclerosis. This is the first evidence that eliciting an immune response to CETP can inhibit the development of atherosclerosis.

Such endogenously produced antibodies against an individual's own CETP is advantageous over other possible therapeutic approaches. For example, use of polypeptide inhibitors of CETP, such as one recently isolated from baboons (see, e.g., WO 93/11782; Kushwaha, R. S., et al., *J. Lipid Res.*, 34: 1285–1297 (1993); *Genetic Engineering News*, 14: 44 (1994); *Science*, 262: 1974–1975 (1993)), or infusion of exogenously produced (foreign) anti-CETP-antibodies which inhibit CETP activity, are both likely to elicit an immune reaction directed against such foreign CETP inhibitory molecules. Such an immune response could rapidly inactivate and/or clear from the body the exogenously supplied CETP inhibitor. Theoretically, such an immune response against the exogenously supplied CETP inhibitor could be overcome by administering increasing doses of the inhibitor. However, multiple administrations of doses of a foreign CETP inhibitor, particularly multiple doses of ever-increasing amounts of such foreign molecules, presents the possibility of a hypersensitivity reaction, endangering the health of the individual being treated. Such problems associated with using exogenously produced CETP inhibitors are avoided by using the peptide-based vaccines of this invention, which recruit an individual's own immune system antibodies to specifically inhibit endogenous CETP. Repeated dosing, graduated dosing, and undesirable side-effects (such as a human anti-mouse antibody (HAMA) response) are avoided by employing the anti-CETP vaccine approach described herein.

The CETP vaccine peptide compositions of this invention may be administered by any route used for vaccination, including: parenterally such as intraperitoneally, interperitoneally, intradermally (subcutaneously), intramuscularly, intravenously or orally. Preferably, the vaccines of this invention are administered parenterally, e.g., intraperitoneally, interperitoneally, intradermally, intramuscularly, or intravenously. If oral administration of a vaccine peptide is desired, any pharmaceutically acceptable oral excipient may be mixed with the vaccine peptides of this invention, for example, such as solutions approved for use in the Sabin oral polio vaccine. As with certain other vaccines, such as for tetanus, an occasional booster administration of the CETP vaccine peptide compositions may be necessary to maintain a desired level of modulation or inhibition of endogenous CETP. As noted above, biodegradable microspheres, such as those comprised of poly (DL-lactide-co-glycolide), have been shown to be useful for effective vaccine delivery and immunization via oral or parenteral routes (Eldridge, J. H., et al., In *Immunobiology of Proteins and Peptides V: Vaccines: Mechanisms, Design, and Applications*, Atassi M. Z., ed. (Plenum Press, New York, 1989), pp. 191–202).

Appropriate dosages of the peptide vaccines of this invention are established by general vaccine methodologies used in the art based on measurable parameters for which the vaccine is proposed to affect, including monitoring for potential contraindications, such as hypersensitivity reaction, erythema, induration, tenderness (see, e.g., *Physician's Desk Reference. 49th ed.*, (Medical Economics Data Production Co., Mont Vale, N.J., 1995), pp.1628, 2371 (referring to hepatitis B vaccine), pp. 1501, 1573, 1575 (referring to measles, mumps, and/or rubella vaccines), pp. 904, 919, 1247, 1257, 1289, 1293, 2363 (referring to diphtheria, tetanus and/or pertussis vaccines)) ; Talwar, G. P., et al., *Proc. Natl. Acad. Sci. USA*, 91: 8532–8536 (1994)). A common and traditional approach for vaccinating humans is to administer an initial dose of a particular vaccine to sensitize the immune system and then follow up by one or more "booster" doses of the vaccine to elicit an anamnestic response by the immune system that was sensitized by the initial administration of the vaccine (vaccination). Such a "primary and booster" administration procedure has been well known and commonly used in the art, as for example, in developing and using measles, polio, tetanus, diphtheria, and hepatitis B vaccines.

Initially, the amount of a vaccine peptide administered to an individual may be that required to neutralize the approximate level of endogenous CETP activity present in the individual prior to vaccination, as can be determined by measuring CETP activity in serum or plasma samples from the individual, for example as determined using a commercially available CETP assay (e.g., Diagnescent Technologies, Inc., Yonkers, N.Y.). Plasma or serum samples from a vaccinated individual can also be monitored to determine whether a measurable increase in the levels of total HDL or HDL-C is seen after administration of the vaccine peptide using commercially available assays (e.g., available from Wako Chemicals USA, Inc., Richmond, Va.).

A rise in the concentration (titer) of circulating anti-CETP antibodies can be measured in plasma or serum samples, for example using an ELISA assay (see, e.g., Example 3). Thus, it is possible and recommended that initially it be established whether a rise in anti-CETP antibody can be correlated with an increase in the level of HDL or HDL-C, or with a decrease in CETP activity. Thereafter, one need only monitor a rise in titer of anti-CETP antibody to determine whether a sufficient dosage of vaccine peptide has been administered or whether a "booster" dose is indicated to elicit an elevated level of anti-CETP antibody. This is the common procedure with various established vaccinations, such as vaccination against hepatitis B virus.

Three-dimensional arterial imaging methods are currently available which can be used to identify arterial lesions and monitor their development or regression in an individual (see, for example, McPherson, *Scientific American Science & Medicine*, pages 22–31, (March/April, 1996)). Thus such imaging methods can be used to monitor the effectiveness of vaccination with a peptide of this invention.

A more complete appreciation of this invention and the advantages thereof can be obtained from the following non-limiting examples.

EXAMPLES

Example 1

Design and Synthesis of an Anti-CETP Vaccine Peptide

To investigate the possibility of eliciting an antibody response against endogenous CETP, a peptide was prepared having a helper T cell epitope portion comprising a universal tetanus toxoid helper T cell epitope and a B cell epitope portion comprising a carboxyl terminal region of human CETP. A 31-amino acid peptide was designed having the amino acid sequence C Q Y I K A N S K F I G I T E F G F P E H L L V D F L Q S L S (SEQ ID NO:2), in which Q Y I K A N S K F I G I T E (amino acids 2to 15 of SEQ ID NO:2) is the same amino acid sequence as amino acids 830 to 843 of the tetanus toxoid protein, F G F P E H L L V D F L Q S L S (amino acids 16 to 31 of SEQ ID NO:2) is the same amino acid sequence as amino acids 461 to 476 SEQ ID NO:4 containing the neutral lipid transfer domain of human CETP and known to be recognized by anti-human CETP Mab TP2 (Wang, S., et al., *J. Biol. Chem.*, 267: 17487–17490 (1992); Wang, S., et al., *J. Biol. Chem.*, 268: 1955–1959 (1993)), and the amino terminal cysteine (C) residue is present for use in linking the peptide to itself or other molecules if desired. The CETP-related portion of this synthetic peptide differs from the corresponding portion of rabbit CETP amino acid sequence only at the glutamic acid (E) residue (see, Nagashima. M., et al., *J. Lipid Res.*, 29: 1643–6149 (1988) (cloning of rabbit CETP gene)). However, prior study has indicated anti-human CETP Mabs can recognize this corresponding region of rabbit CETP (see, Hesler, C. B., et al., *J. Biol. Chem.*, 263: 5020–5023 (1988)). The peptide was synthesized to order using standard peptide synthesis methods by Quality Controlled Biochemicals, Inc. (Hopkinton, Mass.).

Example 2

Immunization of Rabbits against Endogenous CETP

The synthetic vaccine peptide (SEQ ID NO:2) of Example 1 above was injected into New Zealand White Rabbits to test the ability of the vaccine peptide to elicit an immune response against endogenous rabbit CETP. Group I contained three rabbits (rb#1–#3), each of which was subjected to a protocol for administration of the vaccine peptide. Group II contained one rabbit (rb#4) as a control that was not treated.

The general protocol for testing the vaccine peptide in the rabbits is shown in FIG. 1. On Day 1, peptide (100 μg) was suspended in the RIBI™ adjuvant system (RIBI ImmunoChem Research, Inc., Hamilton. Mont.) according to manufacturer's instructions to a final volume of 1000 μl, and each rabbit of Group I was injected at two intramuscular sites (250 μl per site), subcutaneously at two sites (100 μl per site), and six intradermal sites (50 μl per site). On Day 28, a boost (100 μg of peptide in RIBI™ adjuvant system) was administered as on Day 1. On Day 56, another boost (100 μg of peptide in RIBI™ adjuvant system) was administered as on Day 1.

Blood samples (approximately 1–5 ml) were withdrawn from the ear of each rabbit prior to each initial injection ("prebleed") and on Days 42, 70, and 108, except that there was no pre-bleed for control rabbit rb#4. Blood plasma samples were prepared by standard centrifugation methods to separate cellular components from the plasma. Plasma samples were stored at −70° C. Plasma samples of both Groups I and II were analyzed for presence of and increase in titer of anti-CETP antibodies and for total plasma cholesterol and plasma HDL-C levels.

Example 3

Figure 2:
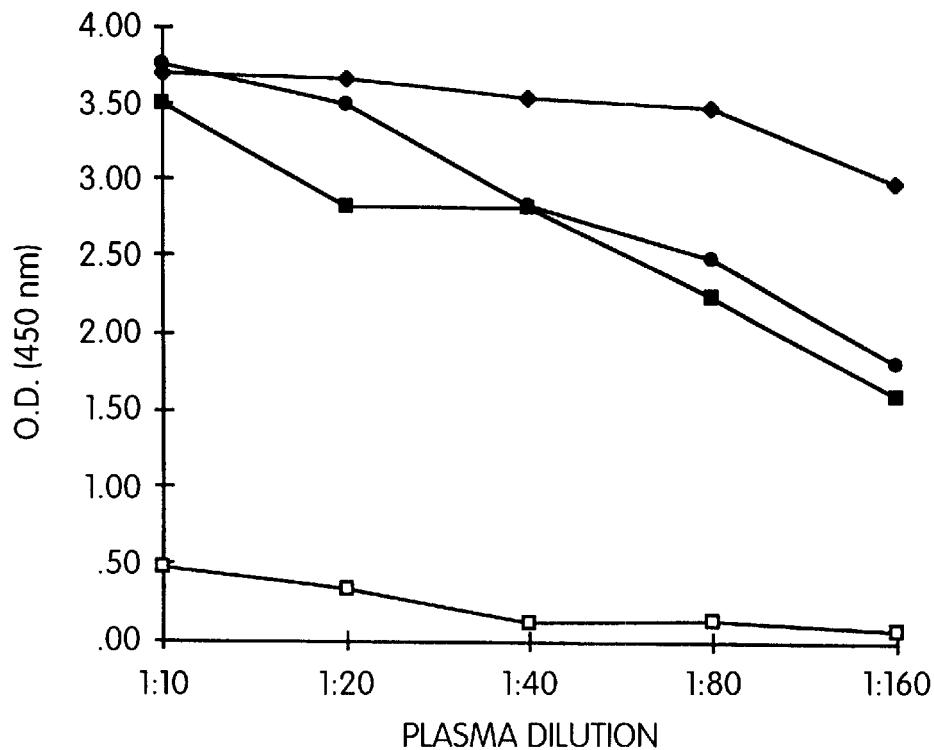
FIG. 2. Optical density (O.D.) at 450 nm versus plasma dilution based on ELISA for anti-CETP antibody binding to recombinant CETP in diluted plasma samples taken from rabbits (rb#1–#44) on Day 70. Open square (rabbit rb#4) refers to the plasma of a rabbit not administered the vaccine peptide (control). Solid square, circle, and diamond refer to rabbits rb#1, #2, and #3, respectively, which were administered a vaccine peptide having the amino acid sequence of SEQ ID NO:2.

Production of Anti-CETP Antibody in Vaccinated Rabbits Direct ELISA for Titering Anti-CETP Antibodies A sandwich enzyme-linked immunosorbent assay (ELISA) was used to titer plasma samples containing anti-CETP antibody. In this set-up, recombinant human CETP (human rCETP, obtained from recombinant CHO cell line CHO(AT) licensed from The Trustees of Columbia University, New York, N.Y.) was adsorbed to wells of a microtiter dish, and various dilutions of rabbit plasma from the rabbits of Groups I and II were added to each well. Each well of a NUNC Maxisorb 96-well plate was coated by overnight exposure at 4° C. to 100 μl of a 1 μg/ml solution of human rCETP in PBS. Non-specific binding was blocked by adding a 1% solution of BSA in PBS and 0.05% Tween to each well and incubating for 2 hours at room temperature (20°–22° C.) on a rotating shaker at 150 rpm. The wells were then washed four times with ELISA wash buffer (PBS+ 0.05% Tween). Plasma samples were then diluted 1:10 in dilution buffer (1% BSA in PBS), followed by 6 two-fold serial dilutions in the same buffer. Diluted samples (100 μl) were added to the wells, incubated for 2 hours at room temperature on a rotating shaker at 150 rpm, and then washed 4 times with ELISA wash buffer (PBS+0.05% Tween). To detect bound anti-CETP antibodies, 100 μl of a 1:10,000 dilution of horseradish peroxidase (HRP) labeled goat anti-rabbit immunoglobulin (Southern Biotechnology Associates, Inc.; Birmingham, Ala.) in dilution buffer was added, and the plates were incubated for 2 hours at room temperature on a rotating shaker at 150 rpm. The wells were then washed four times with ELISA wash buffer (see above), peroxidase substrate TMB (TMB peroxidase substrate, Kirkegaard & Perry Laboratories, Inc., Gaithersburg, Md.) added, and the plates were incubated 30 minutes at room temperature. Change in optical density was monitored spectrophotometrically at 450 nm using an ELISA reader (e.g., E-max, Molecular Device Corp., Menlo Park, Calif.). In this assay, the O.D. was directly proportional to the amount of anti-CETP antibodies present in the plasma samples. The results indicated that all of the rabbits (rb#1–rb#3) of Group I produced anti-CETP antibody which was specific for recombinant human CETP. No anti-CETP antibody was produced in the untreated control rabbit (rb#4) of Group I in Example 2. See FIG. 2.

Competitive ELISA for Detecting Anti-CETP Antibody

This assay was designed to determine if the vaccinated rabbits had generated antibodies that bind to the same epitope as the anti-CETP Mab TP2 (licensed from The Trustees of Columbia University, New York, N.Y.). A standard competitive ELISA was adapted to detect the presence of anti-CETP antibodies in rabbit plasma. In this assay, horseradish peroxidase (HRP) was conjugated to the anti-CETP Mab TP2 which specifically binds to the 26 amino acid carboxyl terminal fragment of human CETP (Wang et al., J. Biol. Chem., 267: 17487–17490 (1992); Wang et al., J. Biol. Chem., 268: 1955–1959 (1993)).

The following method was used to conjugate HRP to antibody. Antibody was dialyzed against $Na_2CO_3$ (50 mM, pH 9.5). The dialyzed antibody was at a concentration of 2 to 5 mg/ml. HRP (Boehringer-Mannheim) was dissolved in sodium acetate buffer (1.0 mM, pH 4.4) to a concentration of 6 mg/ml. The HRP was then activated by adding 0.2 ml of sodium periodate (21.4 mg/ml acetate buffer, made immediately before use) to every 1 ml of HRP solution, and the activation mixture was incubated at room temperature on a rocker for 20 minutes. The activated HRP was then passed over a G25 column equilibrated with acetate buffer to desalt the activated HRP. An optical density (O.D.) at 403 nm corresponds to approximately 1 mg HRP/ml. The desalted, activated HRP was then added to the dialyzed antibody at an amount equal to one half the amount of antibody (by weight, for example, for every 1 mg of IgG, add 0.5 mg activated HRP), and the mixture was incubated for 2 hours at room temperature on a rocker to allow the HRP to conjugate to the antibody molecules. The conjugation reaction was stopped by adding 20 µl of sodium borohydride (10 mg/ml) for every 1 ml of the HRP-antibody conjugation mixture, and the mixture was then incubated on ice for 30 minutes. The HRP-conjugated antibody mixture was dialyzed overnight against phosphate buffered saline (PBS) and then centrifuged (Airfuge) for 15 minutes at 30 psi. Thimerosal was added to the supernatant (HRP-conjugated antibody) to 0.5%, and bovine serum albumin was added to 1%. The HRP-conjugated antibody preparation was stored at 4° C. and protected from light.

Wells of 96-well microtiter plate were coated with CETP by incubating in each well 100 µl of a 300 ng/ml solution of recombinant human CETP (obtained from the recombinant CHO cell line CHO(AT), licensed from The Trustees of Columbia University, New York, N.Y.) in phosphate buffered saline (PBS). The wells were drained and the wells were filled with a 1% (wt/wt) solution of bovine serum albumin (BSA) in PBS and 0.05% (vol./vol.) Tween (Sigma Chemical Co., St. Louis, Mo.) and incubated for 2 hours at room temperature on a rotating shaker (approximately 150 rpm) to block non-specific binding. The wells were washed four times with ELISA wash buffer (PBS+0.05% Tween), and 100 µl of plasma samples diluted in dilution buffer (1% BSA in PBS) was added. The plates were then incubated for 1 hour at room temperature on a rotating shaker as above, and then washed four times with ELISA wash buffer. To each well was next added 100 µl of a 1:100,000 dilution of horseradish peroxidase-conjugated (labeled) Mab TP2 in dilution buffer. The plates were incubated for 1 hour at room temperature on a rotating shaker as above, then washed four times with ELISA wash buffer. The horseradish peroxidase substrate (e.g., TMB peroxidase substrate, Kirkegaard & Perry Laboratories, Inc., Gaithersburg, Md.) was added to each well and a change in optical density (O.D.) at 450 nm was monitored spectrophotometrically using an ELISA reader (e.g., E-max, Molecular Devices Corp., Menlo Park, Calif.). In this assay, if antibody was produced against the CETP-related portion of the vaccine peptide, such unlabeled anti-CETP antibody molecules present in the plasma samples competes with the labeled TP2 Mab for binding to the CETP adsorbed on the walls of the wells and an inhibition in color development is observed as the concentration of plasma sample increases (i.e., O.D. is inversely proportional to the amount of anti-CETP antibody present in each plasma sample).

Figure 3:
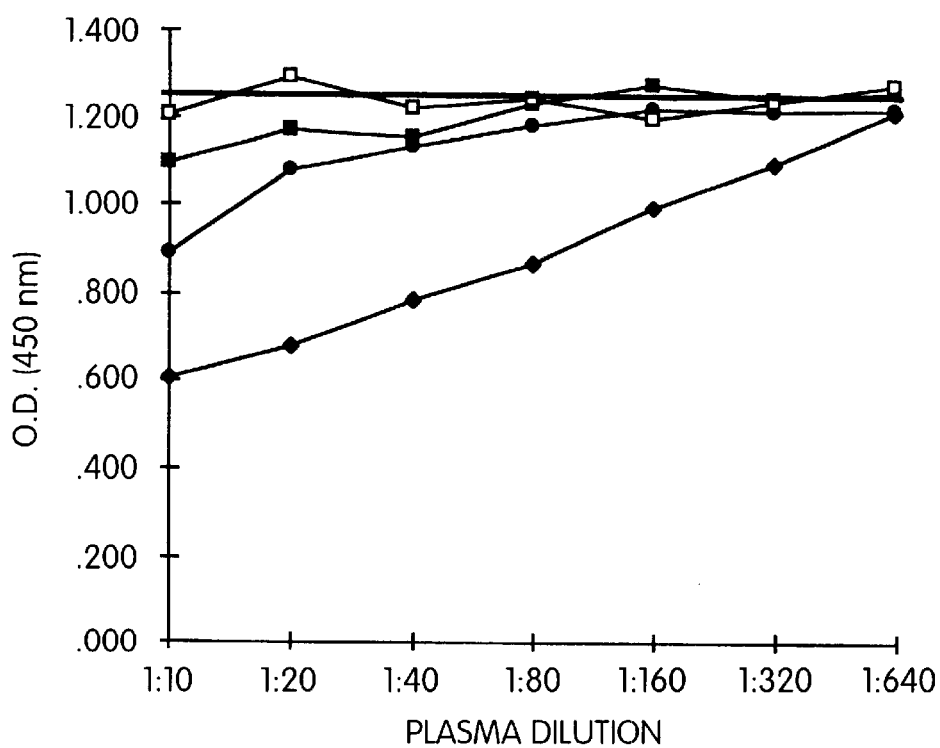
FIG. 3. Optical density (O.D.) at 450 nm versus plasma dilution for blood plasma samples from rabbits (rb#1–#4, see description of FIG. 2, above) based on competitive ELISA for inhibition of monoclonal antibody (Mab) TP2 binding to recombinant human CETP by anti-CETP antibody in diluted rabbit blood plasma samples taken on Day 70.

As shown in FIG. 3, such inhibition of TP2 binding to CETP was observed in plasma sample from two of the three rabbits that were administered the vaccine peptide. thereby indicating production of CETP-specific antibody (compare graphs of rabbit sera rb#2 and rb#3 with plasma of untreated control rabbit rb#4 in FIG. 3). The strongest inhibition of TP2 binding to CETP was exhibited by plasma of rabbit rb#3 (see FIG. 3).

Example 4

Cholesterol and HDL Levels in Plasma Samples of Vaccinated Rabbits

Figure 4:
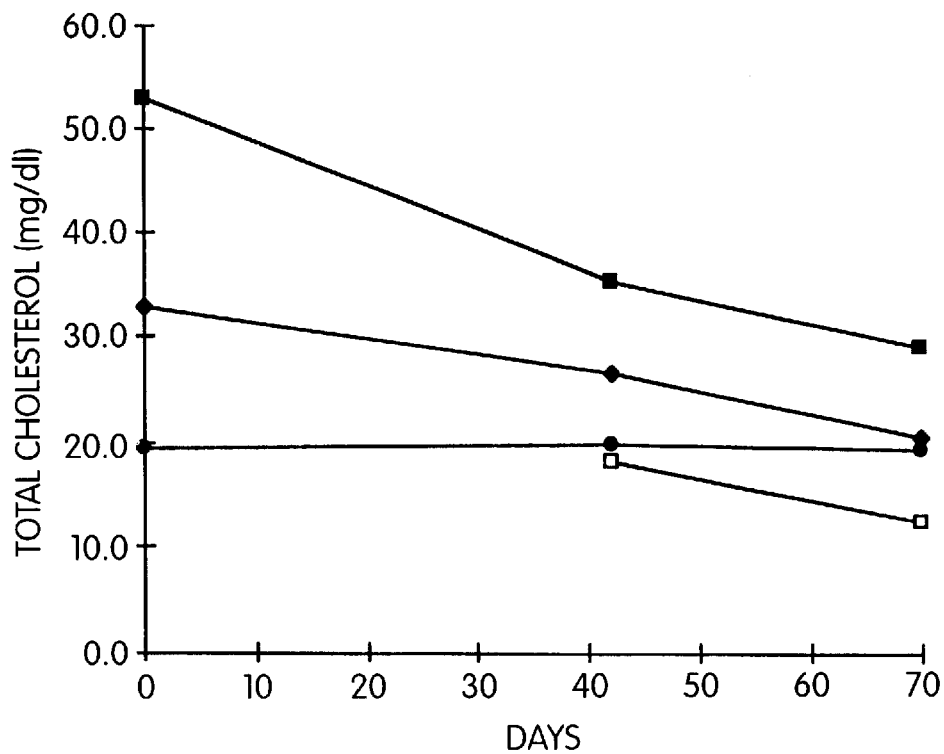
FIG. 4. Concentration of total cholesterol (mg/dl) in plasma samples of rabbits (rb#1–#4, see description of FIG. 2, above) versus time (Days) in vaccination protocol.
Figure 5:
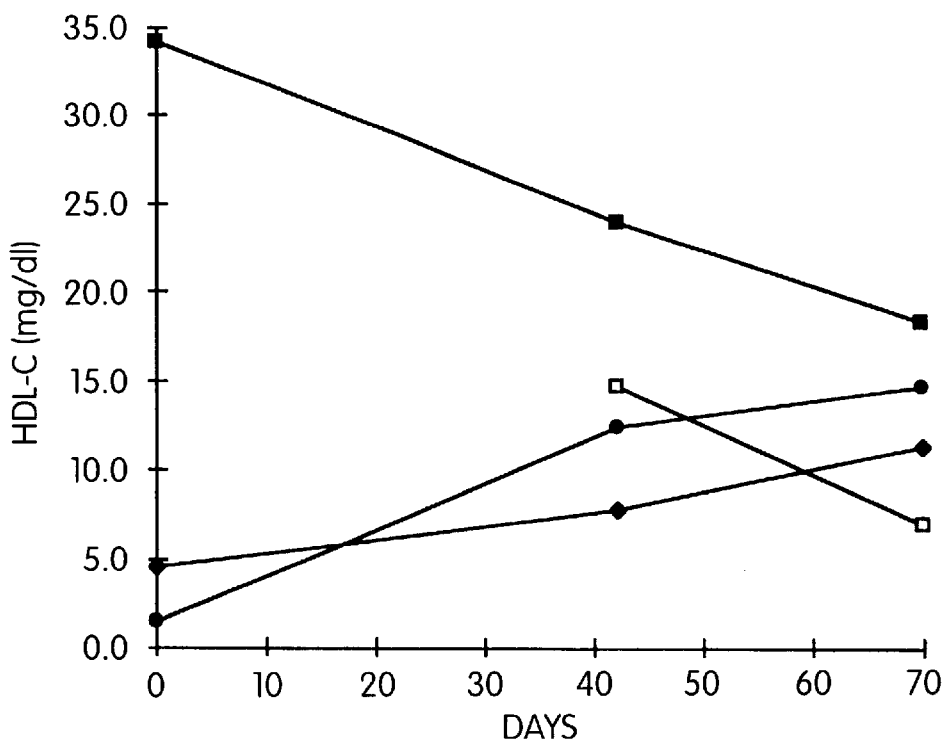
FIG. 5. Concentration of HDL-C (mg/dl) in plasma samples of rabbits (rb#1–#4, see description of FIG. 2, above) versus time (Days) in vaccination protocol.

The plasma samples taken from rabbits of Groups I and II in Example 2 at various times (days) in the vaccination protocol were also assayed for the concentration of total cholesterol (FIG. 4) and HDL-C (FIG. 5). Total plasma cholesterol and HDL-C levels were determined using standard commercial assays (Wako Chemicals USA, Inc., Richmond, Va.). The plasma samples of two rabbits (rb#2 and rb#3) that had the highest anti-CETP antibody titers showed a 2 to 5-fold increase in HDL-C concentrations at Day 70 compared to prebleed plasma samples. Rabbits #2 and #3 also showed increasing plasma HDL concentrations over time compared to the control rabbit (rb#4) and the lowest antibody titer rabbit (rb#1) both of which exhibited decreasing HDL concentrations over time (FIG. 5).

Figure 6:
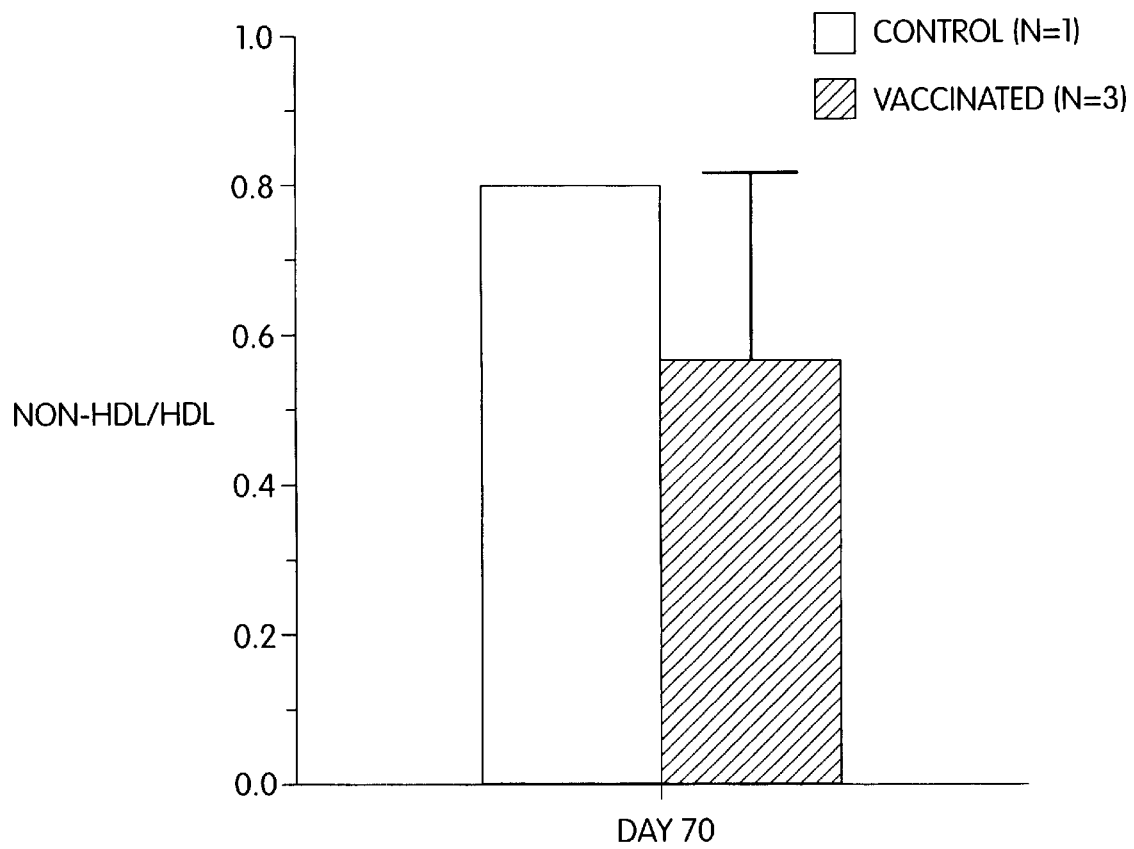
FIG. 6. Ratio Non-HDL/HDL in New Zealand white rabbits on Day 70. Control non-vaccinated rabbit (N=1) rb#4 (solid bar); average (N=3) of vaccinated rabbits rb# 1, 2, and 3 (hatched).

FIG. 6 shows the ratio of Non-HDL cholesterol (Non-HDL) to HDL-cholesterol (HDL) on Day 70 post-vaccination. The data show a trend toward an anti-atherogenic profile in the vaccinated rabbit group (hatched) compared to the non-vaccinated (solid) rabbit. Although no significant difference in total cholesterol in plasma samples was observed, the ratio of Non-HDL/HDL generally declined with a rise in anti-CETP antibody levels in the vaccinated rabbits of Group I.

Example 5

Administration to Transgenic Mice Expressing Human CETP

A strain of transgenic mice that expresses human CETP has recently become commercially available (Biodigm™-CETP mice; Pharmakon USA, Waverly, Pa.). Such mice express human CETP in their livers and are reported to have approximately 50 percent lower levels of HDL-associated cholesterol than non-transgenic litter mates when fed a normal chow diet. Such transgenic animals serve as an additional experimental model to further test vaccine peptides of this invention.

Two groups consisting of six transgenic CETP-expressing mice were used to test the same vaccine peptide used in Examples 1 to 4 above. Each mouse of Group I received primary injections of the vaccine peptide dissolved in phosphate buffered saline (PBS) and emulsified with complete Freund's adjuvant (1:1) to yield a final concentration of 100 μg/100 μl. Each mouse was administered the vaccine peptide mixture in a 50 μl dose (50 μg) at each of two subcutaneous sites. On Day 28 and again on Day 56, the animals were similarly administered boosts of the peptide vaccine (100 μg) in PBS, except the vaccine peptide was emulsified with Incomplete Freund's adjuvant. Samples of blood were withdrawn on Day 42 and Day 63. The mice of control Group II received primary and boost injections of PBS emulsified with adjuvant, but without vaccine peptide, in the same manner as the Group I mice. Plasma samples were prepared as described above for the rabbit plasma samples.

Figure 7:
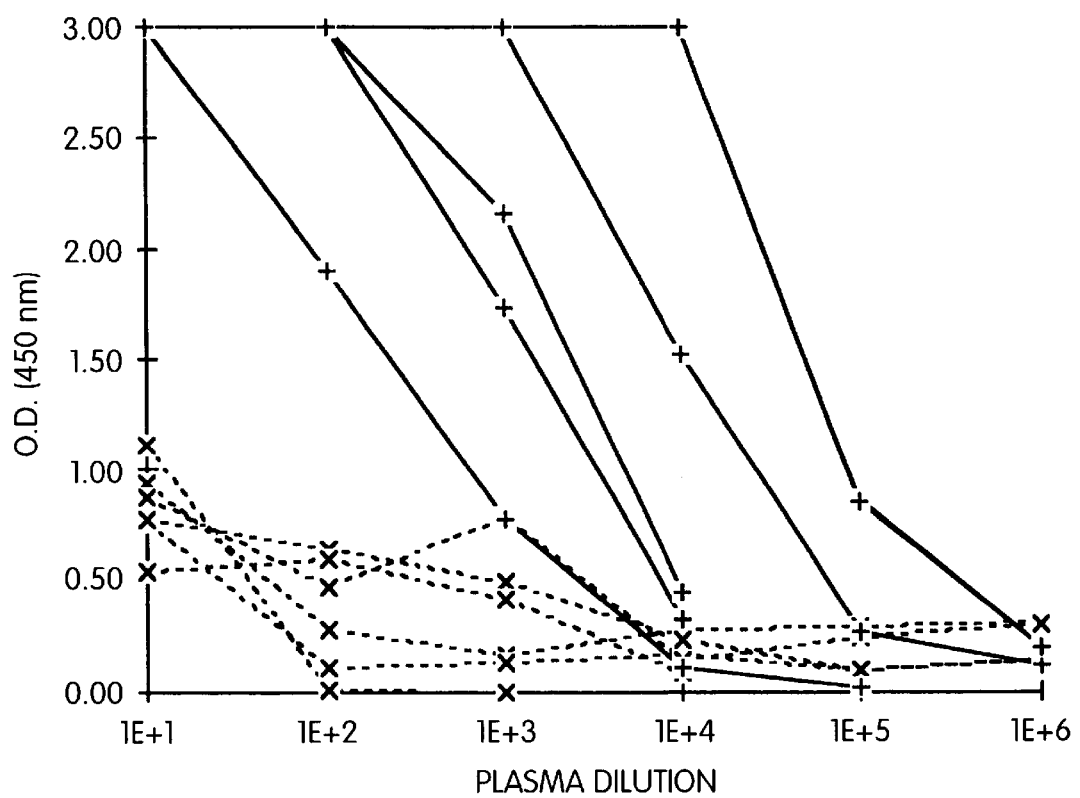
FIG. 7. Optical density (O.D.) at 450 nm versus plasma dilution (semi-logarithmic graph) based on ELISA for anti-CETP antibody binding to recombinant CETP in diluted plasma samples taken from human CETP-transgenic mice on Day 70 in the vaccination protocol. The data for each mouse administered a vaccine peptide having the amino acid sequence of SEQ ID NO:2 is indicated by "+" and a solid line. Data for each control mouse is indicated by "×" and a dashed line. Plasma dilutions spanned a range of 1:10 to 1:1,000,000 (1E+1 to 1E+6).

All Group I mice had significant titers of anti-CETP antibody as measured in a wide range of plasma dilutions (1:10 to 1:1,000,000) by direct ELISA as described above (see FIG. 7). Furthermore, three of the six mice from Group I were also shown to have anti-CETP antibody that competed with Mab TP2 for binding to recombinant human CETP (as was found for rabbits rb#2 and rb#3 in Example 3, above).

Example 6

Immunization of Rabbits against Endogenous CETP in a Cholesterol-Fed Model of Atherosclerosis The synthetic vaccine peptide (SEQ ID NO:2) of Example 1 above was injected into New Zealand White Rabbits to test the ability of the vaccine peptide to elicit an immune response against endogenous rabbit CETP and to protect or reduce development of atherosclerosis. Group I contained six rabbits (rb#1–#6), each of which was subjected to a protocol for administration of the vaccine peptide. Control Group II contained six rabbits (rb#7–12) that were vaccinated but not fed a high cholesterol diet. Control Group III contained six rabbits (rb#13–18) that were not vaccinated and not fed a high cholesterol diet. Control Group IV contained six rabbits (rb#19–24) that were not vaccinated but fed a high cholesterol diet. The high cholesterol diet was administered starting four weeks after a final boost with the vaccine and continued for a total of 17 weeks.

The general protocol for testing the vaccine peptide in the rabbits is shown in Table 1 below. On Day 0, peptide (100 μg) was suspended in the RIBI™ adjuvant system (RIBI ImmunoChem Research, Inc., Hamilton, Mont.) according to manufacturer's instructions to a final volume of 1000 μl, and each rabbit of Group I and II were injected at two intramuscular sites (250 μl per site), subcutaneously at two sites (100 μl per site), and six intradermal sites (50 μl per site). On Day 28, a boost (100 μg of peptide in RIBI™ adjuvant system) was administered as on Day 0. On Day 49, another boost (100 μg of peptide in RIBI™ adjuvant system) was administered as on Day 0. On Day 77, Groups I and IV were fed 0.25% (w/w) cholesterol-enriched diets (rabbit chow supplemented with cholesterol (Farmer's Exchange, Framingham, Mass.). Groups II and III were fed the same rabbit chow but not supplemented with cholesterol (Farmer's Exchange, Framingham, Mass.).

Blood samples (approximately 1–5 ml) were withdrawn from the ear of each rabbit prior to each initial injection ("prebleed") and routinely at approximately every two weeks thereafter. Blood plasma samples were prepared by standard centrifugation methods to separate cellular components from the plasma. Plasma samples were stored at −70° C. Plasma samples of all Groups were analyzed for presence of and increase in titer of anti-CETP antibodies and for total plasma cholesterol and plasma HDL-C levels.

TABLE 1

RABBIT SCHEDULE

| WEEK | procedure, by group | | | | CHOW group 2 and 3 | CHOW group 1 and 4 | WEEKS/DIET | ACTUAL DAY |
|---|---|---|---|---|---|---|---|---|
| | 1 | 2 | 3 | 4 | | | | |
| −2 | B | B | B | B | Normal | Normal | | −14 |
| −1 | B | B | B | B | Normal | Normal | | −6 |
| 0 | B,V | B,V | B | B | Normal | Normal | | 0 |
| 1 | | | | | Normal | Normal | | 7 |
| 2 | B | B | B | B | Normal | Normal | | 14 |
| 3 | | | | | Normal | Normal | | 21 |
| 4 | B,V | B,V | B | B | Normal | Normal | | 28 |
| 5 | | | | | Normal | Normal | | 35 |
| 6 | | | | | Normal | Normal | | 42 |
| 7 | B,V | B,V | B | B | Normal | Normal | | 49 |
| 8 | | | | | Normal | Normal | | 56 |
| 9 | | | | | Normal | Normal | | 63 |
| 10 | B | B | B | B | Normal | Normal | | 70 |
| 11 | | | | | Transition | Transition | 0 | 77 |
| 12 | | | | | control | 0.25% chol | 1 | 84 |
| 13 | B | B | B | B | control | 0.25% chol | 2 | 91 |
| 14 | | | | | control | 0.25% chol | 3 | 98 |
| 15 | B | B | B | B | control | 0.25% chol | 4 | 105 |
| 16 | | | | | control | 0.25% chol | 5 | 112 |
| 17 | B | B | B | B | control | 0.25% chol | 6 | 119 |
| 18 | | | | | control | 0.25% chol | 7 | 126 |
| 19 | B | B | B | B | control | 0.25% chol | 8 | 133 |
| 20 | | | | | control | 0.25% chol | 9 | 140 |
| 21 | B | B | B | B | control | 0.25% chol | 10 | 147 |
| 22 | | | | | control | 0.25% chol | 11 | 154 |
| 23 | B | B | B | B | control | 0.25% chol | 12 | 161 |

TABLE 1-continued

RABBIT SCHEDULE

| | procedure, by group | | | | CHOW | CHOW | | |
| | 1 | 2 | 3 | 4 | group 2 and 3 | group 1 and 4 | | |
| WEEK | | | | | | | WEEKS/DIET | ACTUAL DAY |
|---|---|---|---|---|---|---|---|---|
| 24 | | | | | control | 0.25% chol | 13 | 168 |
| 25 | B | B | B | B | control | 0.25% chol | 14 | 175 |
| 26 | | | | | control | 0.25% chol | 15 | 182 |
| 27 | | | | | control | 0.25% chol | 16 | 189 |
| 28 | B,E | | | B,E | control | 0.25% chol | 17 | 196 |

KEY:
1 = vaccinate, high cholesterol diet
2 = vaccinate, normal/control diet
3 = control, normal/control diet
4 = control, high cholesterol diet
B = blood sample
V = vaccinate
E = euthanize Example 7

Figure 9:
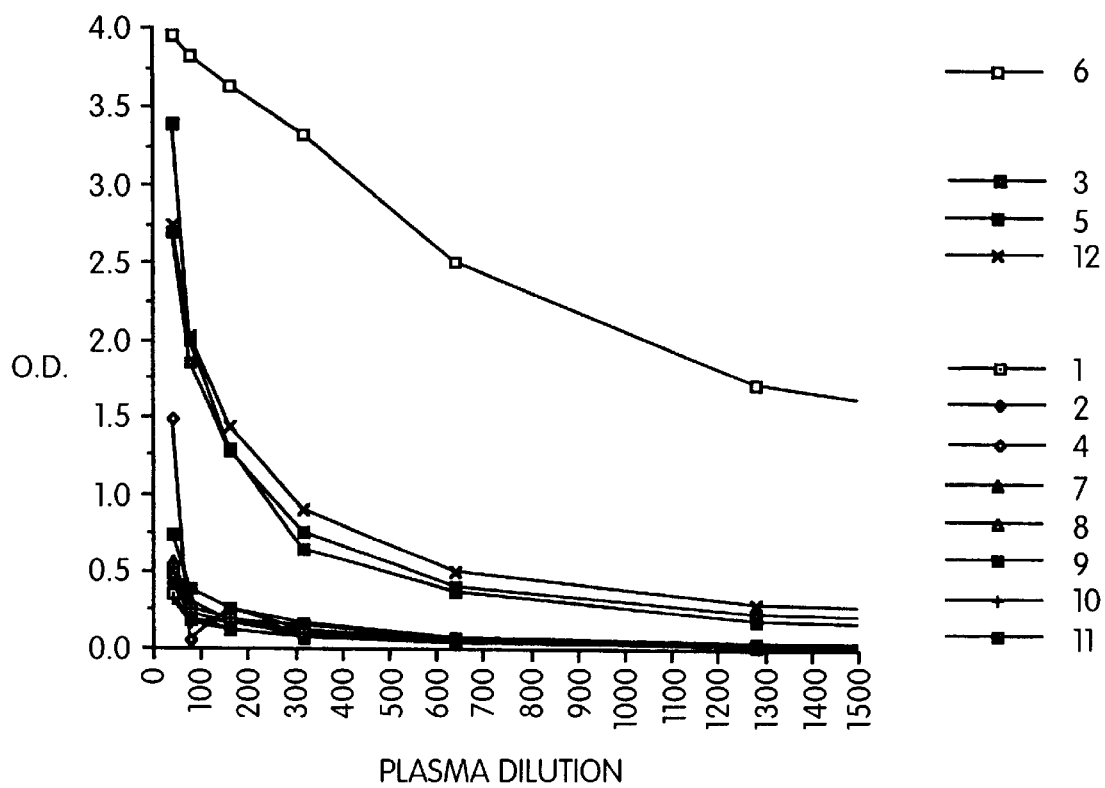
FIG. 9. Antibody titer to recombinant human CETP from Groups I and II of Atherosclerosis Model based on ELISA. OD at 405 nm versus rabbit plasma dilution.

Production of Anti-CETP Antibody in Vaccinated Rabbits in Atherosclerotic (Hypercholesterolemia) Model Direct ELISA for Titering Anti-Recombinant Human CETP Antibodies A sandwich enzyme-linked immunosorbent assay (ELISA) was used to titer plasma samples containing anti-CETP antibody. In this set-up, recombinant human CETP (human rCETP, obtained from recombinant CHO cell line CHO(AT) licensed from The Trustees of Columbia University, New York, N.Y.) was adsorbed to wells of a microtiter dish, and various dilutions of rabbit plasma from the rabbits of Groups I–IV were added to each well. Each well of a NUNC Maxisorb 96-well plate was coated by overnight exposure at 4° C. to 100 µl of a 1 µg/ml solution of human rCETP in PBS. Non-specific binding was blocked by adding a 1% solution of BSA in PBS and 0.05% Tween to each well and incubating for 2 hours at room temperature (20°–22° C.) on a rotating shaker at 150 rpm. The wells were then washed four times with ELISA wash buffer (PBS+0.05% Tween). Plasma samples were then diluted 1:10 in dilution buffer (1% BSA in PBS), followed by 6 two-fold serial dilutions in the same buffer. Diluted samples (100 µl) were added to the wells, incubated for 2 hours at room temperature on a rotating shaker at 150 rpm, and then washed 4 times with ELISA wash buffer (PBS+0.05% Tween). To detect bound anti-CETP antibodies, 100 µl of a 1:10,000 dilution of horseradish peroxidase (HRP) labeled goat anti-rabbit immunoglobulin (Southern Biotechnology Associates, Inc.; Birmingham, Ala.) in dilution buffer was added, and the plates were incubated for 2 hours at room temperature on a rotating shaker at 150 rpm. The wells were then washed four times with ELISA wash buffer (see above), peroxidase substrate TMB (TMB peroxidase substrate, Kirkegaard & Perry Laboratories, Inc., Gaithersburg, Md.) added, and the plates were incubated 30 minutes at room temperature. Change in optical density was monitored spectrophotometrically at 450 nm using an ELISA reader (e.g., E-max, Molecular Device Corp., Menlo Park, Calif.). In this assay, the O.D. was directly proportional to the amount of anti-CETP antibodies present in the plasma samples. The results indicated that five of the twelve vaccinated rabbits (Groups I and II) produced anti-CETP antibody which was specific for recombinant human CETP (see FIG. 9). No anti-recombinant human CETP antibody was produced in the untreated control Groups III and IV.

Direct ELISA for Titering Autoreactive Anti-Rabbit (Endogenous) CETP Antibodies

A peptide (rabbit peptide) containing an amino acid sequence of the endogenous rabbit CETP was synthesized to order using standard peptide synthesis methods by Quality Controlled Biochemicals, Inc. (Hopkinton, Mass.) having the sequence of SEQ ID NO:7: L Q M D F G F P K H L L V D F L Q S L S, which corresponding to amino acids 457 to 476 of the carboxyl terminal region of the human CETP sequence shown in SEQ ID NO:4. This portion of the rabbit CETP amino acid sequence differs from the human CETP sequence in that the glutamic acid residue at position 465 of the human sequence (SEQ ID NO:4) is replaced with a lysine residue (see amino acid 9 in SEQ ID NO:7). For the purposes of this assay the rabbit peptide was purchased as a biotinylated derivative (biotin covalently attached to the amino terminal leucine residue).

Preblocked streptavidin-coated microtiter plates were prepared as follows. One hundred µl of 5 µg/ml streptavidin (catalog #43-4302, Zymed Laboratories, Inc., S. San Francisco, Calif.) in PBS was dispensed into each well of 96-well microplates with removable strips (catalog #950-2950-00P, LabSystems, Needham, Mass.), sealed and incubated at room temperature overnight. Following aspiration of the contents of each well the plates were washed and then blocked with 300 µl of PBS containing 1% BSA, 5% sucrose, 0.05% Tween 20 and 0.1% gentamicin sulfate, overnight at room temperature. The following day the wells were emptied and allowed to dry overnight before storing, sealed with desiccant, at 4° C., until use. Rabbit peptide was then added to each well (100 µl of 1 µg/ml solution in PBS (GIBCO BRL) supplemented with 10% (w/v) bovine serum albumin (BSA)) and incubated for 1 hour with shaking at 150 rpm at room temperature (22° C.). Plates were washed three times with Wash Buffer (PBS supplemented with 0.05% Tween-20) to remove unbound peptide. Rabbit plasma samples were diluted (initially 1:40, then serially by half thereafter) in PBS supplemented with 5% BSA and 1% gelatin and 100 µl of each dilution were incubated for 90 minutes at room temperature with shaking at 150 rpm. Plates were then washed three times with Wash Buffer. Goat-anti-rabbit IgG labelled with horseradish peroxidase (Southern Biotechnology Associates, Inc., Birmingham, Ala.) was diluted 1:5000 in Wash Buffer and 100 µl added to each well which were then incubated for 90 minutes at room temperature with shaking at 150 rpm. The plates were washed three times with Wash Buffer and then incubated with peroxidase substrate TMB (TMB peroxidase substrate, Kirkegaard & Perry Laboratories, Inc., Gaithersburg, Md.) added, and the plates were incubated 30 minutes at room temperature. Change in optical density was monitored spectrophotometrically at 450 nm using an ELISA reader (e.g., E-max, Molecular Device Corp., Menlo Park, Calif.). In this assay, the O.D. was directly proportional to the amount of anti-rabbit CETP antibodies present in the plasma samples.

Figure 10A:
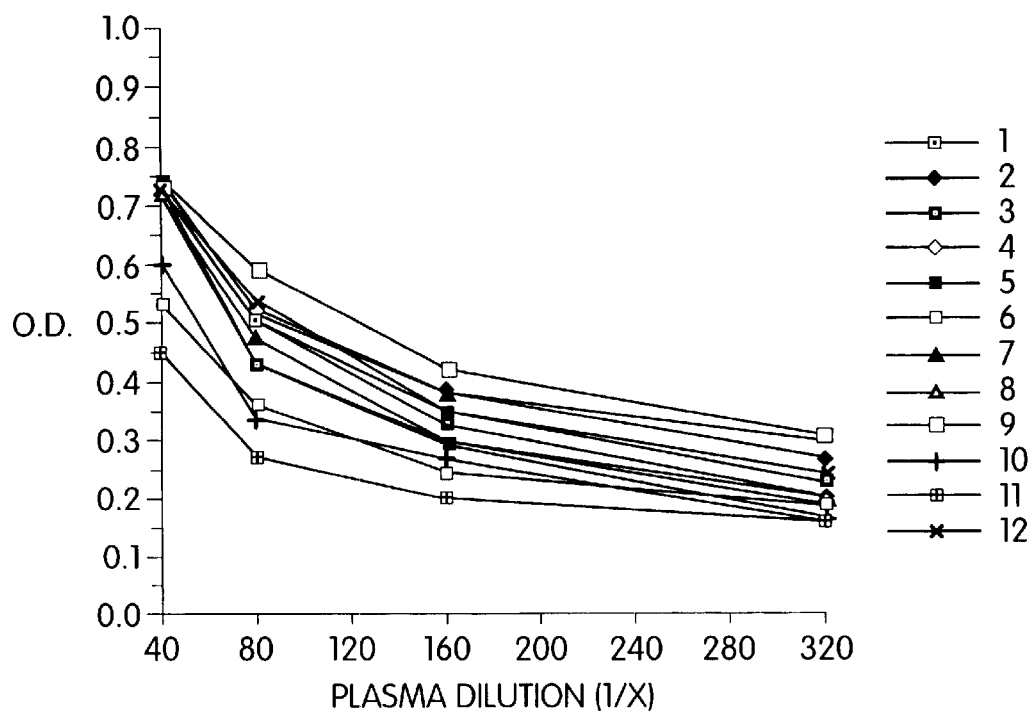
FIGS. 10A and 10B. Rabbit plasma antibody titers to rabbit CETP in Atherosclerosis Model based on ELISA. Pre-vaccination plasma (FIG. 10A). Post-vaccination plasma (FIG. 10B). OD at 405 nm versus rabbit plasma dilution.
Figure 10B:
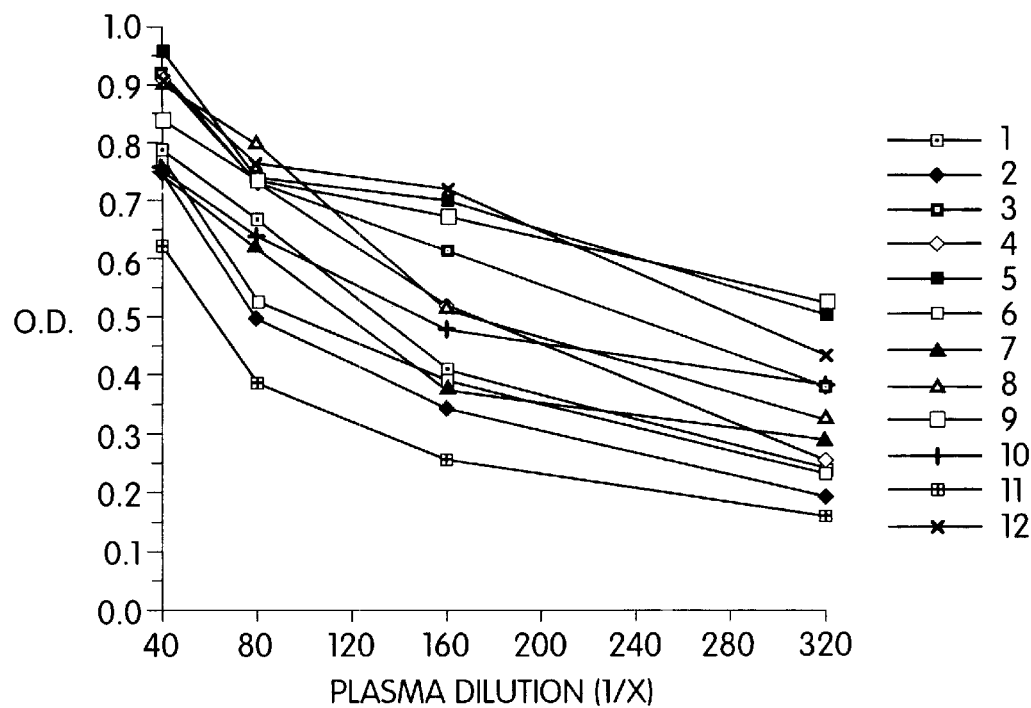

The results indicate that at three weeks post final boost (and prior to administering the cholesterol supplemented diet to Groups I and IV) six of the twelve vaccinated animals (three from each of Groups I and II) produced antibodies that reacted with the peptide derived from the endogenous rabbit CETP sequence (See FIGS. 10A and 10B).

The data showed that the vaccine peptide was capable of eliciting autoreactive antibodies to the rabbit endogenous CETP. This indicates that the combination of the tetanus toxoid T cell epitope and the B cell epitope of the carboxyl terminal region of CETP is capable of breaking tolerance to a specific self protein, i.e., in this case, endogenous rabbit CETP.

Example 9

Figure 11:
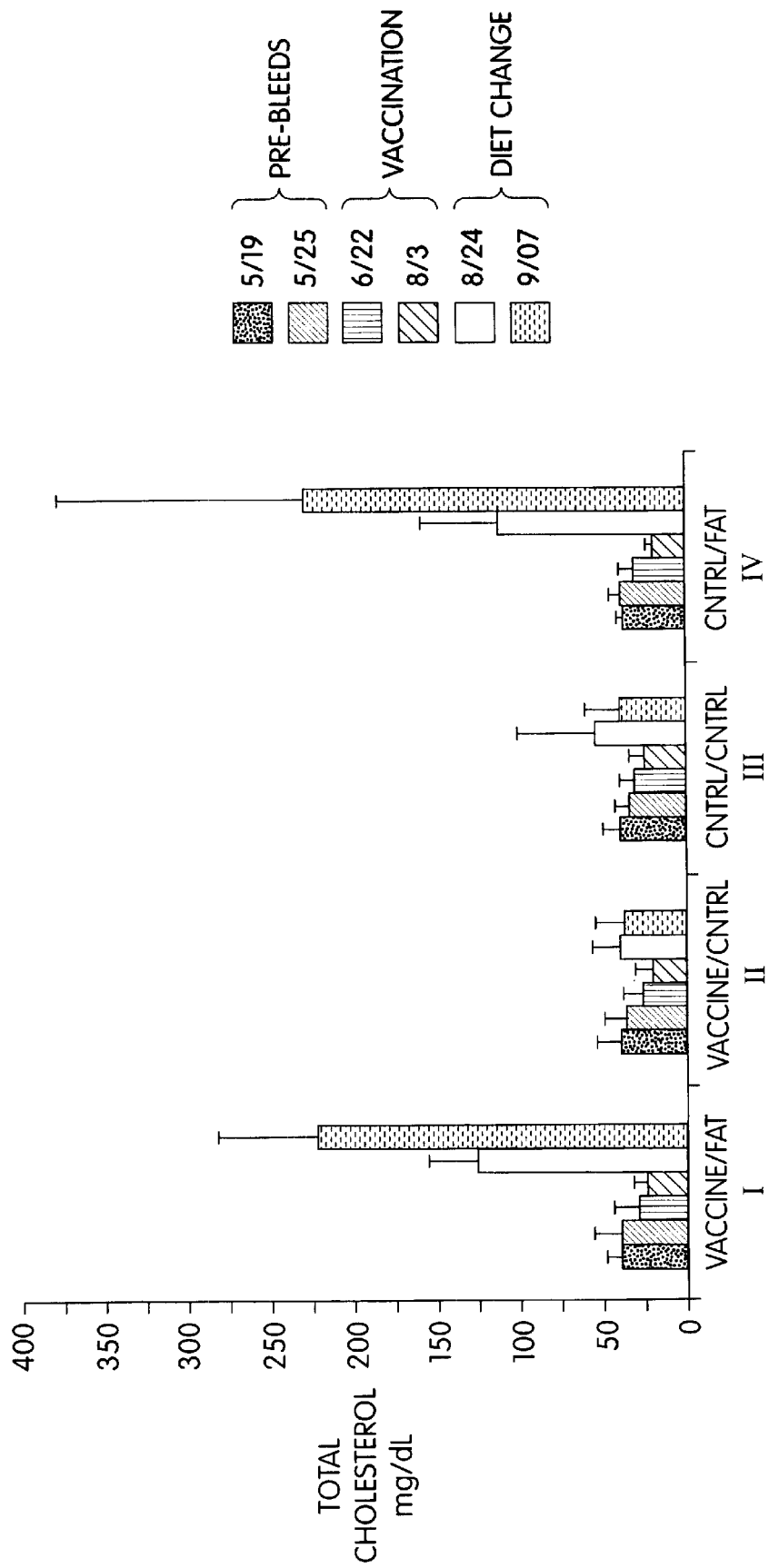
FIG. 11. Total cholesterol in pre- and post-vaccinated animals in Atherosclerosis Model. Total cholesterol (mg/dl) versus day and group.
Figure 12:
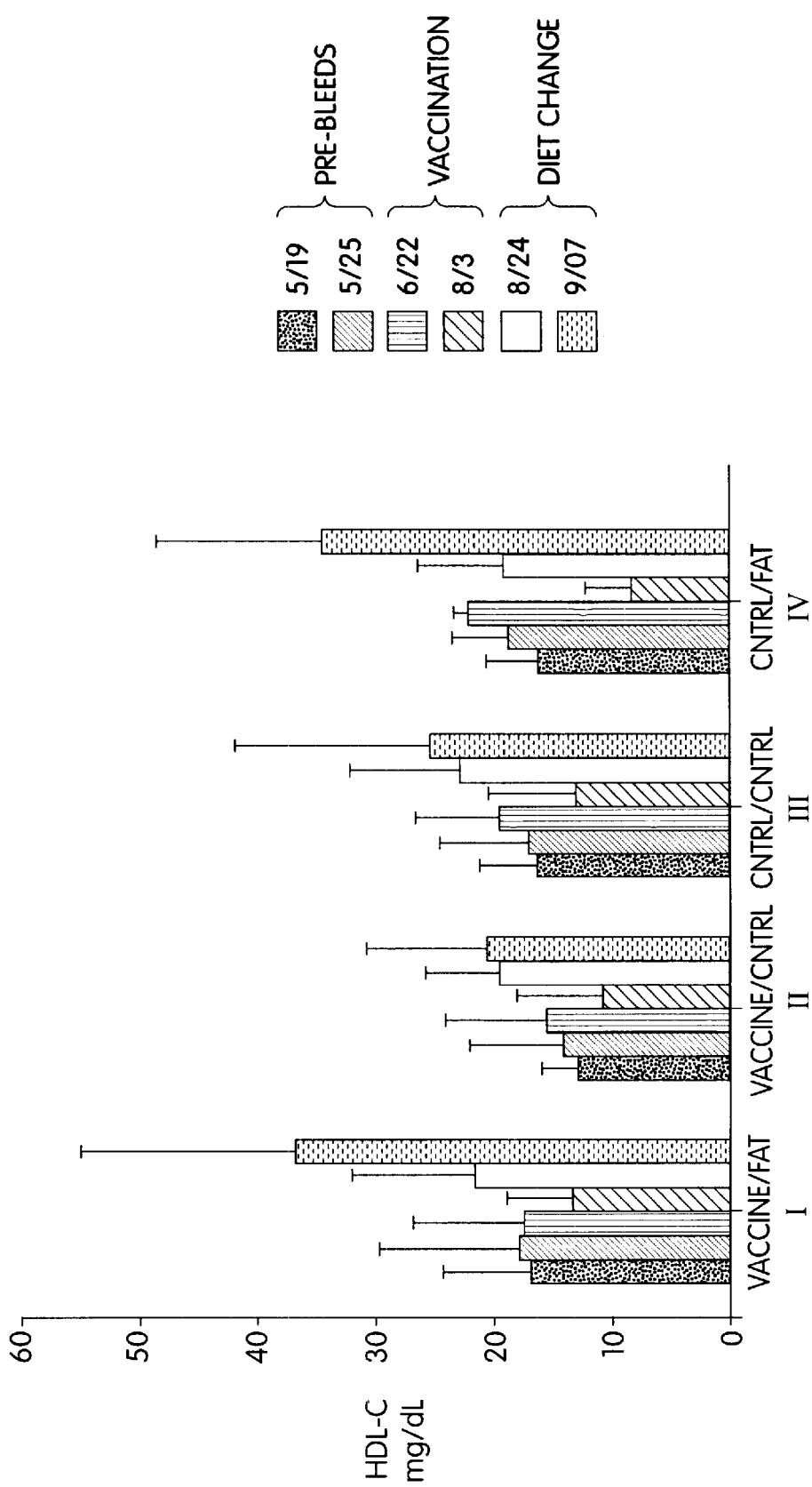
FIG. 12. HDL-C in pre- and post-vaccinated animals in Atherosclerosis Model. HDL-C (mg/dl) versus day and group.

Cholesterol and HDL Levels in Plasma Samples of Vaccinated Rabbits in Atherosclerotic Model The plasma samples taken from rabbits of Groups in Example 6 at various times (days) in the vaccination protocol were also assayed for the concentration of total cholesterol (FIG. 11) and HDL-C (FIG. 12). Total plasma cholesterol and HDL-C levels were determined using standard commercial assays (Wako Chemicals USA, Inc., Richmond, Va.).

The plasma samples of Groups I (vaccinated) and IV (non-vaccinated) showed an increase (hypercholesterolemia) in total cholesterol due to administration of the cholesterol supplemented diet (FIG. 11). Groups II (vaccinated) and III (non-vaccinated) did not exhibit diet-induced hypercholesterolemia (FIG. 11).

Similarly, Groups I and IV fed the cholesterol supplemented diet showed an increase in HDL-C (FIG. 12). Preliminary analysis of the data for Group II, indicated that the three animals with the highest anti-CETP antibody titers also showed an increase in their levels of HDL-C compared to pre-vaccination levels. The preliminary analysis also indicated that in three of the five animals in Group III, no significant change in the levels of HDL-C were observed compared to pre-vaccination levels.

Example 10

Measurement of Aortic Atherosclerotic Lesions in Rabbits in a Cholesterol-Fed Model of Atherosclerosis Aortas were removed from all surviving rabbits (four in Groups I and IV, five in Group II, six in Group III) after 17 weeks (Day 196 from primary vaccination) on cholesterol supplemented diet in Groups I and IV and control diet (no cholesterol supplement) in Groups II and III. Death of the non-surviving rabbits was shown by necropsy to be due to hair balls and not, therefore. experimental design. Each aorta was opened for an enface view to examine for atherosclerotic lesions. The full length of the aorta, i.e., from the aortic arch in the heart to the bifurcation in the lower abdomen, was stained with Oil Red O to detect lesions. The lesions were measured and the data quantitated using a computer program (The Morphometer, Woods Hole Educational Associated, Woods Hole, Mass.).

Figure 13:
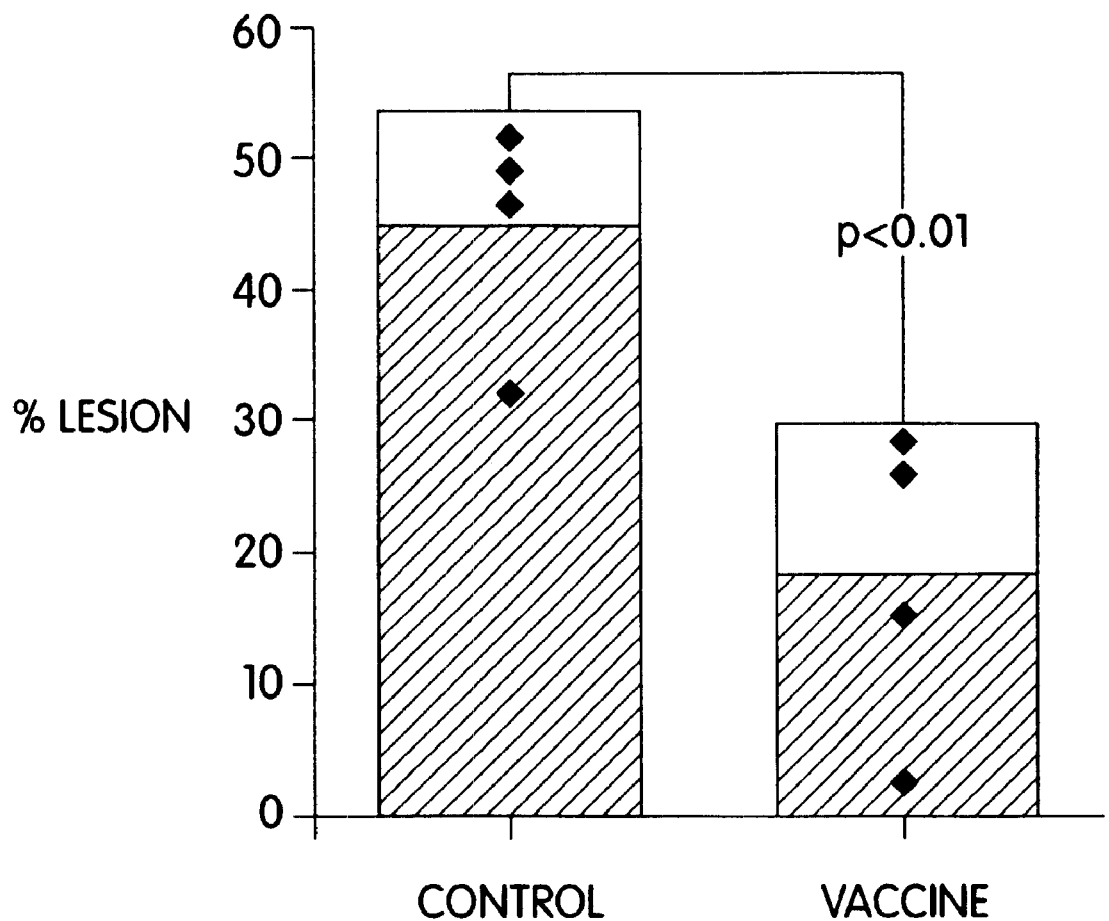
FIG. 13. Bar graphs of the average percent of total area of aorta covered by atherosclerotic lesions in vaccinated and control rabbits on cholesterol supplemented diets. Individual data points (diamonds), average percent of aortic area covered by lesions (shaded bar), standard deviation of data points (open bar), p <0.01 indicates statistical significance between bar graphs.

The results in FIG. 13 of this analysis demonstrated a statistically significant reduction in the size of lesions in animals of Group I (vaccinated, cholesterol-supplemented diet) as compared to the size of lesions in animals in Group IV (non-vaccinated, cholesterol-supplemented diet). The results showed that the peptide vaccine was capable of reducing the area of atherosclerotic lesions in animals fed cholesterol supplemented (hypercholesterolemic) diets by greater than 50%. Non-vaccinated animals (Group IV) had lesions that covered an average of 45% of the total area of the aorta, whereas vaccinated animals (Group I) had lesions that covered an average of 19% of the total area of the aorta.

Although a number of embodiments have been described above, it will be understood by those skilled in the art that modifications and variations of the described compositions and methods may be made without departing from either the spirit of the invention or the scope of the appended claims. The articles and publications cited herein are incorporated by reference.

What is claimed is:

1. A method of elevating the ratio of circulating HDL to circulating LDL, VLDL, or total cholesterol in a human or other animal comprising administering to the human or animal a vaccine composition comprising a peptide conjugate comprising a helper T cell epitope portion linked to a B cell epitope portion, wherein said B cell epitope portion comprises a B cell epitope of a CETP of a human or other animal, and said peptide conjugate, when administered to said human or other animal, elicits production of endogenous antibodies that specifically bind endogenous CETP and results in an elevation of the ratio of circulating HDL to circulating LDL, VLDL, or total cholesterol in said human or other animal.

2. A method according to claim 1 wherein said B cell epitope portion comprises between six and 26 consecutive amino acids of the carboxyl terminal 26 amino acids of human CETP (SEQ ID NO:1).

3. The method according to claim 1 wherein the helper T cell epitope portion of the peptide conjugate comprises a T cell epitope selected from the group consisting of the amino acid sequence of amino acids 830 to 843 of tetanus toxin protein (amino acids 2 to 16 of SEQ ID NO:2) and the amino acid sequence of amino acids 947 to 967 of tetanus toxin protein of SEQ ID NO:3.

4. The method according to claim 1 wherein the B cell epitope portion of the peptide conjugate is selected from the group consisting of between six and 26 consecutive amino acids of SEQ ID NO:1.

5. The method according to claim 1 wherein the peptide conjugate further comprises an amino terminal cysteine residue.

6. A method of decreasing the level of endogenous CETP activity in a human or other animal comprising administering to the human or animal a peptide conjugate comprising a helper T cell epitope portion linked to a B cell epitope portion comprising a B cell epitope of a CETP of a human or animal, wherein said peptide conjugate, when administered to said human or animal, elicits production of endogenous antibodies that specifically bind endogenous CETP and results in a decrease in the level of endogenous CETP activity in said human or animal.

7. The method according to claim 6 wherein the peptide conjugate is administered in an amount sufficient to elicit production in said human or other animal of anti-CETP antibodies.

8. A method of altering the catabolism of HDL-cholesterol to decrease the development of atherosclerotic lesions in a human or other animal comprising administering to the human or animal a peptide conjugate comprising a helper T cell epitope portion linked to a B cell epitope portion, said helper T cell epitope portion comprising a broad range T cell epitope and said B cell epitope portion comprising a B cell epitope of CETP, wherein said peptide conjugate, when administered to said human or animal, elicits production of endogenous antibodies that specifically bind endogenous CETP and results in a decrease in the development of atherosclerotic lesions in said human or animal compared to a human or animal not receiving such treatment.

9. A method of increasing the level of circulating HDL in a human or other animal comprising administering to the human or animal a peptide conjugate comprising a helper T cell epitope portion and a B cell epitope portion, wherein said B cell epitope portion comprises a B cell epitope of a CETP of a human or other animal, and wherein said peptide conjugate, when administered to said human or animal, elicits production of endogenous antibodies that specifically bind endogenous CETP and results in an increase in the level of circulating HDL in said human or animal.

10. The method according to claim 9, wherein the helper T cell epitope portion comprises a helper T cell epitope derived from an antigenic peptide selected from the group consisting of tetanus toxoid, diphtheria toxoid, pertussis vaccine, Bacile Calmette-Guerin (BCG), polio vaccine, measles vaccine, mumps vaccine, rubella vaccine, purified protein derivative of tuberculin, keyhole limpet hemocyanin, and combinations thereof.

11. The method according to claim 9, wherein the B cell epitope portion comprises a carboxyl terminal region of human CETP consisting of between six and 26 consecutive amino acids of SEQ ID NO:1.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 26 amino acids
        (B) TYPE:amino acid
        (D) TOPOLOGY: linear (ii) MOLECULE TYPE:peptide (iii) HYPOTHETICAL:

(iv) ANTI-SENSE:

(ix) FEATURE:

(A) NAME/KEY:Carboxyl terminal 26 amino
            acids of human CETP
        (B) LOCATION:

(x) PUBLICATION INFORMATION:
        (A) AUTHORS:Drayna, Dennis, et al.
        (B) TITLE:Cloning and sequencing of human cholesteryl ester
            transfer cDNA
        (C) JOURNAL:Nature
        (D) VOLUME:327
        (E) ISSUE:
        (F) PAGES:632-634
        (G) DATE:18-JUN-1987
        (K) RELEVANT RESIDUES IN SEQ ID NO:1: FROM 1 TO 26

(xi) SEQUENCE DESCRIPTION: SEQ ID NO: 1:

Arg  Asp  Gly  Phe  Leu  Leu  Leu  Gln  Met  Asp  Phe
 1              5                        10

Gly  Phe  Pro  Glu  His  Leu  Leu  Val  Asp  Phe  Leu
              15                        20

Gln  Ser  Leu  Ser
              25

(2) INFORMATION FOR SEQ ID NO:2:

(i) SEQUENCE CHARACTERISTICS:
        (A) LENGTH:31 amino acids
        (B) TYPE:  amino acid
        (D) TOPOLOGY:  linear (ii) MOLECULE TYPE: peptide (iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO: 2:

Cys  Gln  Tyr  Ile  Lys  Ala  Asn  Ser  Lys  Phe  Ile
 1              5                        10

Gly  Ile  Thr  Glu  Phe  Gly  Phe  Pro  Glu  His  Leu
              15                        20

Leu  Val  Asp  Phe  Leu  Gln  Ser  Leu  Ser
              25                        30

(2) INFORMATION FOR SEQ ID NO:3:

(i) SEQUENCE CHARACTERISTICS:
        (A) LENGTH: 21 amino acids
        (B) TYPE:  amino acid
        (D) TOPOLOGY:  linear (ii) MOLECULE TYPE: peptide (iii) HYPOTHETICAL:

(iv) ANTI-SENSE:

(ix) FEATURE:
        (A) NAME/KEY:  21-amino acid tetanus toxoid universal helper T
            cell epitope.
        (B) LOCATION:

(x) PUBLICATION INFORMATION:
        (A) AUTHORS:Panina-Bordignon, P., et al.
        (B) TITLE:Universally immunogenic T cell epitopes: promiscuous
            binding to human MHC class
        (C) JOURNAL:European Journal of Immunology (D) VOLUME:19
        (E) ISSUE:
        (F) PAGES:2237-2242
        (G) DATE:1989
        (K) RELEVANT RESIDUES IN SEQ ID NO:3: FROM 1 TO 21

(xi) SEQUENCE DESCRIPTION: SEQ ID NO: 3:

```
Phe  Asn  Asn  Phe  Thr  Val  Ser  Phe  Trp  Leu  Arg
1                   5                        10

Val  Pro  Lys  Val  Ser  Ala  Ser  His  Leu  Glu
              15                   20
```

(2) INFORMATION FOR SEQ ID NO: 4:

(i) SEQUENCE CHARACTERISTICS:
        (A) LENGTH: 476 amino acids
        (B) TYPE:amino acid
        (D) TOPOLOGY: linear (ii) MOLECULE TYPE:peptide (iii) HYPOTHETICAL:

(iv) ANTI-SENSE:

(ix) FEATURE:
        (A) NAME/KEY:Amino acid sequence of mature
            human CETP
        (B) LOCATION:

(x) PUBLICATION INFORMATION:
        (A) AUTHORS:Drayna, Dennis, et al.
        (B) TITLE:Cloning and sequencing of human cholesteryl ester
            transfer cDNA
        (C) JOURNAL:Nature
        (D) VOLUME:327
        (E) ISSUE:
        (F) PAGES:632-634
        (G) DATE:18-JUN-1987
        (K) RELEVANT RESIDUES IN SEQ ID NO:1: FROM 1 TO 476

(xi) SEQUENCE DESCRIPTION: SEQ ID NO: 4:

```
Cys  Ser  Lys  Gly  Thr  Ser  His  Glu  Ala  Gly  Ile  Val  Cys
1                   5                        10

Arg  Ile  Thr  Lys  Pro  Ala  Leu  Leu  Val  Leu  Asn  His  Glu
         15                   20                   25

Thr  Ala  Lys  Val  Ile  Gln  Thr  Ala  Phe  Gln  Arg  Ala  Ser
                   30                   35

Tyr  Pro  Asp  Ile  Thr  Gly  Glu  Lys  Ala  Met  Met  Leu  Leu
40                            45                   50

Gly  Gln  Val  Lys  Tyr  Gly  Leu  His  Asn  Ile  Gln  Ile  Ser
              55                   60                        65

His  Leu  Ser  Ile  Ala  Ser  Ser  Gln  Val  Glu  Leu  Val  Glu
                   70                   75

Ala  Lys  Ser  Ile  Asp  Val  Ser  Ile  Gln  Asn  Val  Ser  Val
         80                   85                   90

Val  Phe  Lys  Gly  Thr  Leu  Lys  Tyr  Gly  Tyr  Thr  Thr  Ala
                   95                   100

Trp  Trp  Leu  Gly  Ile  Asp  Gln  Ser  Ile  Asp  Phe  Glu  Ile
105                      110                      115

Asp  Ser  Ala  Ile  Asp  Leu  Gln  Ile  Asn  Thr  Gln  Leu  Thr
              120                      125                130

Cys  Asp  Ser  Gly  Arg  Val  Arg  Thr  Asp  Ala  Pro  Asp  Cys
                   135                      140
```

-continued

```
Tyr Leu Ser Phe His Lys Leu Leu His Leu Gln Gly
    145                 150                 155
Glu Arg Glu Pro Gly Trp Ile Lys Gln Leu Phe Thr Asn
            160                 165
Phe Ile Ser Phe Thr Leu Lys Leu Val Leu Lys Gly Gln
170                 175                 180
Ile Cys Lys Glu Ile Asn Val Ile Ser Asn Ile Met Ala
            185                 190                 195
Asp Phe Val Gln Thr Arg Ala Ala Ser Ile Leu Ser Asp
                200                 205
Gly Asp Ile Gly Val Asp Ile Ser Leu Thr Gly Asp Pro
    210                 215                 220
Val Ile Thr Ala Ser Tyr Leu Glu Ser His His Lys Gly
                225                 230
His Phe Ile Tyr Lys Asn Val Ser Glu Asp Leu Pro Leu
235                 240                 245
Pro Thr Phe Ser Pro Thr Leu Leu Gly Asp Ser Arg Met
            250                 255                 260
Leu Tyr Phe Trp Phe Ser Glu Arg Val Phe His Ser Leu
                265                 270
Ala Lys Val Ala Phe Gln Asp Gly Arg Leu Met Leu Ser
    275                 280                 285
Leu Met Gly Asp Glu Phe Lys Ala Val Leu Glu Thr Trp
            290                 295
Gly Phe Asn Thr Asn Gln Glu Ile Phe Gln Glu Val Val
300                 305                 310
Gly Gly Phe Pro Ser Gln Ala Gln Val Thr Val His Cys
            315                 320                 325
Leu Lys Met Pro Lys Ile Ser Cys Gln Asn Lys Gly Val
                330                 335
Val Val Asn Ser Ser Val Met Val Lys Phe Leu Phe Pro
    340                 345                 350
Arg Pro Asp Gln Gln His Ser Val Ala Tyr Thr Phe Glu
            355                 360
Glu Asp Ile Val Thr Thr Val Gln Ala Ser Tyr Ser Lys
365                 370                 375
Lys Lys Leu Phe Leu Ser Leu Leu Asp Phe Gln Ile Thr
            380                 385                 390
Pro Lys Thr Val Ser Asn Leu Thr Glu Ser Ser Ser Glu
                395                 400
Ser Ile Gln Ser Phe Leu Gln Ser Met Ile Thr Ala Val
    405                 410                 415
Gly Ile Pro Glu Val Met Ser Arg Leu Glu Val Val Phe
            420                 425
Thr Ala Leu Met Asn Ser Lys Gly Val Ser Leu Phe Asp
430                 435                 440
Ile Ile Asn Pro Glu Ile Ile Thr Arg Asp Gly Phe Leu
            445                 450                 455
Leu Leu Gln Met Asp Phe Gly Phe Pro Glu His Leu Leu
                460                 465
Val Asp Phe Leu Gln Ser Leu Ser
    470                 475
```

(2) INFORMATION FOR SEQ ID NO: 5:

(i) SEQUENCE CHARACTERISTICS:
        (A) LENGTH: 1428 base pairs
        (B) TYPE:nucleic acid
        (C) STRANDEDNESS: single
        (D) TOPOLOGY: linear (ii) MOLECULE TYPE:cDNA (iii) HYPOTHETICAL:

(iv) ANTI-SENSE:

(ix) FEATURE:
        (A) NAME/KEY:Coding sequence for mature human CETP
        (B) LOCATION:

(x) PUBLICATION INFORMATION:
        (A) AUTHORS:Drayna, Dennis, et al.
        (B) TITLE:Cloning and sequencing of human cholesteryl ester
            transfer cDNA
        (C) JOURNAL:Nature
        (D) VOLUME:327
        (E) ISSUE:
        (F) PAGES:632-634
        (G) DATE:18-JUN-1987
        (K) RELEVANT RESIDUES IN SEQ ID NO:5: FROM 1 TO 1428

(xi) SEQUENCE DESCRIPTION: SEQ ID NO:5:

```
TGCTCCAAAG GCACCTCGCA CGAGGCAGGC ATCGTGTGCC                    40

GCATCACCAA GCCTGCCCTC CTGGTGTTGA ACCACGAGAC                    80

TGCCAAGGTG ATCCAGACCG CCTTCCAGCG AGCCAGCTAC                   120

CCAGATATCA CGGGCGAGAA GGCCATGATG CTCCTTGGCC                   160

AAGTCAAGTA TGGGTTGCAC AACATCCAGA TCAGCCACTT                   200

GTCCATCGCC AGCAGCCAGG TGGAGCTGGT GGAAGCCAAG                   240

TCCATTGATG TCTCCATTCA GAACGTGTCT GTGGTCTTCA                   280

AGGGGACCCT GAAGTATGGC TACACCACTG CCTGGTGGCT                   320

GGGTATTGAT CAGTCCATTG ACTTCGAGAT CGACTCTGCC                   360

ATTGACCTCC AGATCAACAC ACAGCTGACC TGTGACTCTG                   400

GTAGAGTGCG GACCGATGCC CCTGACTGCT ACCTGTCTTT                   440

CCATAAGCTG CTCCTGCATC TCCAAGGGGA GCGAGAGCCT                   480

GGGTGGATCA AGCAGCTGTT CACAAATTTC ATCTCCTTCA                   520

CCCTGAAGCT GGTCCTGAAG GGACAGATCT GCAAAGAGAT                   560

CAACGTCATC TCTAACATCA TGGCCGATTT TGTCCAGACA                   600

AGGGCTGCCA GCATCCTTTC AGATGGAGAC ATTGGGGTGG                   640

ACATTTCCCT GACAGGTGAT CCCGTCATCA CAGCCTCCTA                   680

CCTGGAGTCC CATCACAAGG GTCATTTCAT CTACAAGAAT                   720

GTCTCAGAGG ACCTCCCCCT CCCCACCTTC TCGCCCACAC                   760

TGCTGGGGGA CTCCCGCATG CTGTACTTCT GGTTCTCTGA                   800

GCGAGTCTTC CACTCGCTGG CCAAGGTAGC TTTCCAGGAT                   840

GGCCGCCTCA TGCTCAGCCT GATGGGAGAC GAGTTCAAGG                   880

CAGTGCTGGA GACCTGGGGC TTCAACACCA ACCAGGAAAT                   920

CTTCCAAGAG GTTGTCGGCG GCTTCCCCAG CCAGGCCCAA                   960
```

```
GTCACCGTCC ACTGCCTCAA GATGCCCAAG ATCTCCTGCC              1000

AAAACAAGGG AGTCGTGGTC AATTCTTCAG TGATGGTGAA              1040

ATTCCTCTTT CCACGCCCAG ACCAGCAACA TTCTGTAGCT              1080

TACACATTTG AAGAGGATAT CGTGACTACC GTCCAGGCCT              1120

CCTATTCTAA GAAAAAGCTC TTCTTAAGCC TCTTGGATTT              1160

CCAGATTACA CCAAAGACTG TTTCCAACTT GACTGAGAGC              1200

AGCTCCGAGT CCATCCAGAG CTTCCTGCAG TCAATGATCA              1240

CCGCTGTGGG CATCCCTGAG GTCATGTCTC GGCTCGAGGT              1280

AGTGTTTACA GCCCTCATGA ACAGCAAAGG CGTGAGCCTC              1320

TTCGACATCA TCAACCCTGA GATTATCACT CGAGATGGCT              1360

TCCTGCTGCT GCAGATGGAC TTTGGCTTCC CTGAGCACCT              1400

GCTGGTGGAT TTCCTCCAGA GCTTGAGC                           1428
```

(2) INFORMATION FOR SEQ ID NO:6:

(i) SEQUENCE CHARACTERISTICS:
        (A) LENGTH:496 amino acids
        (B) TYPE:amino acid
        (D) TOPOLOGY:linear (ii) MOLECULE TYPE:protein (iii) HYPOTHETICAL:

(iv) ANTI-SENSE:

(ix) FEATURE:
        (A) NAME/KEY:Amino acid sequence for mature rabbit CETP
            protein.
        (B) LOCATION:

(x) PUBLICATION INFORMATION:
        (A) AUTHORS:Nagashima, Mariko, et al.(B) TITLE:Cloning and
            mRNA tissue distribution of rab
        (C) JOURNAL:J. Lipid Res.
        (D) VOLUME:29
        (E) ISSUE:
        (F) PAGES:1643-1649
        (G) DATE:1988
        (K) RELEVANT RESIDUES IN SEQ ID NO:6: FROM 1 TO 496

(xi) SEQUENCE DESCRIPTION: SEQ ID NO:6:

```
Cys Pro Lys Gly Ala Ser Tyr Glu Ala Gly Ile Val Cys
 1               5                  10

Arg Ile Thr Lys Pro Ala Leu Leu Val Leu Asn Gln Glu
        15                  20              25

Thr Ala Lys Val Val Gln Thr Ala Phe Gln Arg Ala Gly
                30                  35

Tyr Pro Asp Val Ser Gly Glu Arg Ala Val Met Leu Leu
40                  45                  50

Gly Arg Val Lys Tyr Gly Leu His Asn Leu Gln Ile Ser
            55                  60                  65

His Leu Ser Ile Ala Ser Ser Gln Val Glu Leu Val Asp
                    70                  75

Ala Lys Thr Ile Asp Val Ala Ile Gln Asn Val Ser Val
        80                  85                  90

Val Phe Lys Gly Thr Leu Asn Tyr Ser Tyr Thr Ser Ala
                95                  100
```

-continued

```
Trp Gly Leu Gly Ile Asn Gln Ser Val Asp Phe Glu Ile
105                 110                115
Asp Ser Ala Ile Asp Leu Gln Ile Asn Thr Glu Leu Thr
        120                 125                130
Cys Asp Ala Gly Ser Val Arg Thr Asn Ala Pro Asp Cys
                135                 140
Tyr Leu Ala Phe His Lys Leu Leu His Leu Gln Gly
145                 150                 155
Glu Arg Glu Pro Gly Trp Leu Lys Gln Leu Phe Thr Asn
            160                 165
Phe Ile Ser Phe Thr Leu Lys Leu Ile Leu Lys Arg Gln
170                 175                 180
Val Cys Asn Glu Ile Asn Thr Ile Ser Asn Ile Met Ala
            185                 190                 195
Asp Phe Val Gln Thr Arg Ala Ala Ser Ile Leu Ser Asp
                200                 205
Gly Asp Ile Gly Val Asp Ile Ser Val Thr Gly Ala Pro
    210                 215                 220
Val Ile Thr Ala Thr Tyr Leu Glu Ser His His Lys Gly
                225                 230
His Phe Thr His Lys Asn Val Ser Glu Ala Phe Pro Leu
235                 240                 245
Arg Ala Phe Pro Pro Gly Leu Leu Gly Asp Ser Arg Met
            250                 255                 260
Leu Tyr Phe Trp Phe Ser Asp Gln Val Leu Asn Ser Leu
                265                 270
Ala Arg Ala Ala Phe Gln Glu Gly Arg Leu Val Leu Ser
    275                 280                 285
Leu Thr Gly Asp Glu Phe Lys Lys Val Leu Glu Thr Gln
            290                 295
Gly Phe Asp Thr Asn Gln Glu Ile Phe Gln Glu Leu Ser
300                 305                 310
Arg Gly Leu Pro Thr Gly Gln Ala Gln Val Ala Val His
    315                 320                 325
Cys Leu Lys Val Pro Lys Ile Ser Cys Gln Asn Arg Gly
            330                 335
Val Val Val Ser Ser Ser Val Ala Val Thr Phe Arg Phe
    340                 345                 350
Pro Arg Pro Asp Gly Arg Glu Ala Val Ala Tyr Arg Phe
            355                 360
Glu Glu Asp Ile Ile Thr Thr Val Gln Ala Ser Tyr Ser
365                 370                 375
Gln Lys Lys Leu Phe Leu His Leu Leu Asp Phe Gln Cys
    380                 385                 390
Val Pro Ala Ser Gly Arg Ala Gly Ser Ser Ala Asn Leu
                395                 400
Ser Val Ala Leu Arg Thr Glu Ala Lys Ala Val Ser Asn
    405                 410                 415
Leu Thr Glu Ser Arg Ser Glu Ser Leu Gln Ser Ser Leu
            420                 425
Arg Ser Leu Ile Ala Thr Val Gly Ile Pro Glu Val Met
430                 435                 440
Ser Arg Leu Glu Val Ala Phe Thr Ala Leu Met Asn Ser
```

```
                445              450              455
Lys Gly Leu Asp Leu Phe Glu Ile Ile Asn Pro Glu Ile
                460              465

Ile Thr Leu Asp Gly Cys Leu Leu Leu Gln Met Asp Phe
        470              475              480

Gly Phe Pro Lys His Leu Leu Val Asp Phe Leu Gln Ser
                485              490

Leu Ser
495
```

(2) INFORMATION FOR SEQ ID NO: 7:

(i) SEQUENCE CHARACTERISTICS:
        (A) LENGTH: 1488 base pairs
        (B) TYPE:nucleic acid
        (C) STRANDEDNESS:single
        (D) TOPOLOGY: linear (ii) MOLECULE TYPE:cDNA (iii) HYPOTHETICAL:

(iv) ANTI-SENSE:

(ix) FEATURE:
        (A) NAME/KEY:
        (B) LOCATION:
        (D) OTHER INFORMATION: Coding sequence for mature
            rabbit CETP (x) PUBLICATION INFORMATION:
        (A) AUTHORS:Nagashima, Mariko, et al.
        (B) TITLE:Cloning and mRNA tissue distribution of rabbit
            cholesteryl ester transfer protein
        (C) JOURNAL:J. Lipid Res.
        (D) VOLUME:29
        (E) ISSUE:
        (F) PAGES:1643-1649
        (G) DATE:1988
        (K) RELEVANT RESIDUES IN SEQ ID NO:7: FROM 1 TO 1488

(xi) SEQUENCE DESCRIPTION: SEQ ID NO: 7:

```
TGTCCCAAAG GCGCCTCCTA CGAGGCTGGC ATCGTGTGTC                    40

GCATCACCAA GCCCGCCCTC TTGGTGTTGA ACCAAGAGAC                    80

GGCCAAGGTG GTCCAGACGG CCTTCCAGCG CGCCGGCTAT                   120

CCGGACGTCA GCGGCGAGAG GGCCGTGATG CTCCTCGGCC                   160

GGGTCAAGTA CGGGCTGCAC AACCTCCAGA TCAGCCACCT                   200

GTCCATCGCC AGCAGCCAGG TGGAGCTGGT GGACGCCAAG                   240

ACCATCGACG TCGCCATCCA GAACGTGTCC GTGGTCTTCA                   280

AGGGGACCCT GAACTACAGC TACACGAGTG CCTGGGGGTT                   320

GGGCATCAAT CAGTCTGTCG ACTTCGAGAT CGACTCTGCC                   360

ATTGACCTCC AGATCAACAC AGAGCTGACC TGCGACGCTG                   400

GCAGTGTGCG CACCAATGCC CCCGACTGCT ACCTGGCTTT                   440

CCATAAACTG CTCCTGCACC TCCAGGGGGA GCGCGAGCCG                   480

GGGTGGCTCA AGCAGCTCTT CACAAACTTC ATCTCCTTCA                   520

CCCTGAAGCT GATTCTGAAG CGACAGGTCT GCAATGAGAT                   560

CAACACCATC TCCAACATCA TGGCTGACTT TGTCCAGACG                   600

AGGGCCGCCA GCATCCTCTC AGATGGAGAC ATCGGGGTGG                   640
```

```
ACATTTCCGT GACGGGGGCC CCTGTCATCA CAGCCACCTA              680

CCTGGAGTCC CATCACAAGG GTCACTTCAC GCACAAGAAC              720

GTCTCCGAGG CCTTCCCCCT CCGCGCCTTC CCGCCCGGTC              760

TTCTGGGGGA CTCCCGCATG CTCTACTTCT GGTTCTCCGA              800

TCAAGTGCTC AACTCCCTGG CCAGGGCCGC CTTCCAGGAG              840

GGCCGTCTCG TGCTCAGCCT GACAGGGGAT GAGTTCAAGA              880

AAGTGCTGGA GACCCAGGGT TTCGACACCA ACCAGGAAAT              920

CTTCCAGGAG CTTTCCAGAG GCCTTCCCAC CGGCCAGGCC              960

CAGGTAGCCG TCCACTGCCT TAAGGTGCCC AAGATCTCCT             1000

GCCAGAACCG GGGTGTCGTG GTGTCTTCTT CCGTCGCCGT             1040

GACGTTCCGC TTCCCCCGCC AGATGGCCGA AGAAGCTGTG             1080

GCCTACAGGT TTGAGGAGGA TATCATCACC ACCGTCCAGG             1120

CCTCCTACTC CCAGAAAAAG CTCTTCCTAC ACCTCTTGGA             1160

TTTCCAGTGC GTGCCGGCCA GCGGAAGGGC AGGCAGCTCA             1200

GCAAATCTCT CCGTGGCCCT CAGGACTGAG GCTAAGGCTG             1240

TTTCCAACCT GACTGAGAGC CGCTCCGAGT CCCTGCAGAG             1280

CTCTCTCCGC TCCCTGATCG CCACGGTGGG CATCCCGGAG             1320

GTCATGTCTC GGCTCGAGGT GGCGTTCACA GCCCTCATGA             1360

ACAGCAAAGG CCTGGACCTC TTCGAAATCA TCAACCCCGA             1400

GATTATCACT CTCGATGGCT GCCTGCTGCT GCAGATGGAC             1440

TTCGGTTTTC CCAAGCACCT GCTGGTGGAT TTCCTGCAGA             1480

GCCTGAGC                                                1488
```

(2) INFORMATION FOR SEQ ID NO:8:

(i) SEQUENCE CHARACTERISTICS:
        (A) LENGTH:50 amino acids
        (B) TYPE: amino acid
        (D) TOPOLOGY: linear (ii) MOLECULE TYPE: peptide (iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO:8 :

```
Cys Gln Tyr Ile Lys Ala Asn Ser Lys Phe Ile Gly Ile
1               5                  10

Thr Glu Leu Phe Pro Arg Pro Asp Gln Gln His Ser Val
            15              20              25

Ala Tyr Thr Phe Glu Glu Asp Ile Phe Gly Phe Pro Glu
                30              35

His Leu Leu Val Asp Phe Leu Gln Ser Leu Ser
40              45              50
```

(2) INFORMATION FOR SEQ ID NO:9:

```
    (i) SEQUENCE CHARACTERISTICS:
        (A) LENGTH:50 amino acids
        (B) TYPE:   amino acid
        (D) TOPOLOGY:  linear (ii) MOLECULE TYPE:  peptide (iii) HYPOTHETICAL:

(iv) ANTI-SENSE:

(ix) FEATURE:
        (A) NAME/KEY:
        (B) LOCATION:

(xi) SEQUENCE DESCRIPTION: SEQ ID NO:9 :

Met Gln Tyr Ile Lys Ala Asn Ser Lys Phe Ile Gly Ile
1               5                   10

Thr Glu Arg Phe Pro Arg Pro Asp Gly Arg Glu Ala Val
        15              20                  25

Ala Tyr Arg Phe Glu Glu Asp Ile Phe Gly Phe Pro Lys
            30              35

His Leu Leu Val Asp Phe Leu Gln Ser Leu Ser
40              45                  50
```